US010000757B2

(12) United States Patent
Naldini et al.

(10) Patent No.: US 10,000,757 B2
(45) Date of Patent: *Jun. 19, 2018

(54) GENE VECTOR

(75) Inventors: Luigi Naldini, Milan (IT); Brian Brown, Milan (IT)

(73) Assignees: OSPEDALE SAN RAFFAELE S.R.L., Milan (IT); FONDAZIONE TELETHON, Rome (IT)

(*) Notice: Subject to any disclaimer, the term of this patent is extended or adjusted under 35 U.S.C. 154(b) by 313 days.

This patent is subject to a terminal disclaimer.

(21) Appl. No.: 11/921,140

(22) PCT Filed: May 26, 2006

(86) PCT No.: PCT/IB2006/002266
§ 371 (c)(1),
(2), (4) Date: May 11, 2009

(87) PCT Pub. No.: WO2007/000668
PCT Pub. Date: Jan. 4, 2007

(65) Prior Publication Data
US 2010/0041737 A1    Feb. 18, 2010

Related U.S. Application Data

(60) Provisional application No. 60/684,954, filed on May 27, 2005.

(51) Int. Cl.
*C12N 15/113* (2010.01)
*C12N 15/63* (2006.01)
*C12N 15/86* (2006.01)
*A61K 48/00* (2006.01)

(52) U.S. Cl.
CPC ........ *C12N 15/1137* (2013.01); *C12N 15/635* (2013.01); *C12N 15/86* (2013.01); *A61K 48/00* (2013.01); *C12N 2310/141* (2013.01); *C12N 2740/15043* (2013.01); *C12N 2740/15045* (2013.01); *C12N 2760/20222* (2013.01); *C12N 2810/6081* (2013.01)

(58) Field of Classification Search
CPC .......................... C12N 15/1137; C12N 15/113
See application file for complete search history.

(56) References Cited

U.S. PATENT DOCUMENTS

| | | | |
|---|---|---|---|
| 9,556,438 B2 * | 1/2017 | Naldini | C12N 15/635 |
| 2005/0059005 A1 | 3/2005 | Tuschl et al. | |
| 2005/0075492 A1 | 4/2005 | Chen et al. | |
| 2005/0266552 A1 * | 12/2005 | Doench et al. | 435/358 |
| 2006/0058266 A1 * | 3/2006 | Manoharan et al. | 514/81 |
| 2006/0200869 A1 | 7/2006 | Naldini et al. | |
| 2006/0265771 A1 | 11/2006 | Lewis et al. | |
| 2007/0054872 A1 | 3/2007 | Reppen et al. | |
| 2009/0004668 A1 * | 1/2009 | Chen et al. | 435/6 |

FOREIGN PATENT DOCUMENTS

| | | |
|---|---|---|
| AU | 2004206232 A1 | 8/2004 |
| EP | 1616012 B1 | 4/2004 |
| JP | S56-169586 A | 12/1981 |
| WO | 9805635 A1 | 2/1998 |
| WO | 9807859 A1 | 2/1998 |
| WO | 9809985 A2 | 3/1998 |
| WO | 9943816 A1 | 9/1999 |
| WO | 9943817 A1 | 9/1999 |
| WO | WO 03/020931 A2 | 3/2003 |
| WO | WO2003/020931 | 3/2003 |
| WO | WO2003020931 | 3/2003 |
| WO | 2003064665 | 8/2003 |
| WO | WO2003/065995 A2 | 8/2003 |
| WO | WO200306465 | 8/2003 |
| WO | WO2004/058749 A1 | 7/2004 |
| WO | 2004065549 A2 | 8/2004 |
| WO | WO2004/066183 A2 | 8/2004 |
| WO | WO 2005013901 | 2/2005 |
| WO | 2005023986 A2 | 3/2005 |

OTHER PUBLICATIONS

Doench et al. (Genes & Development, vol. 18, No. 5, pp. 504-511 (2004).*
Opalinska et al. (Nature Rev., vol. 1: pp. 503-514 (2002).*
Verma et al. (Annu. Rev. Biochem (2005) 74:71-38).*
Chen et al., "MicroRNAs modulate hematopoietic lineage differentiation," *Science*, vol. 303(5654), p. 83-6 (Jan. 2004).
Chen et al., "MicroRNAs as regulators of mammalian hematopoiesis," *Semin Immunol.*, vol. 17(2), p. 155-65 (Apr. 2005).
Lagos-Quintana et al., "Identification of tissue-specific microRNAs from mouse," *Curr. Biol.* vol. 12(9), p. 735-9 (Apr. 30, 2002).
Michael et al., "Reduced accumulation of specific microRNAs in colorectal neoplasia," *Mol. Cancer Res.*, vol. 1(12), p. 882-91 (Oct. 2003).
Kasashima et al., "Altered expression profiles of microRNAs during TPA-induced differentiation of HL-60 cells," *Biochem Biophys Res Commun.*, vol. 322(2), p. 403-10 (Sep. 2004).
Mochizuki et al., "Analysis of a piwi-related gene implicates small RNAs in genome rearrangement in tetrahymena," *Cell*, vol. 110(6), p. 689-99 (Sep. 2002).
Brennecke, Julius, et al. "bantam Encodes a Developmentally Regulated microRNA that Controls Cell Proliferation and Regulates the Proapoptotic Gene hid in *Drosophila*," *Cell* (2003) vol. 113, pp. 25-36.
Brown, Brian D., et al., "Endogenous microRNA regulaion suppresses transgene expression in hematopoietic lineages and enables stable gene transfer," Nature Medicine (2006) vol. 12:5, pp. 585-591.
Johnson, Steven M., et al., "The time of appearance of *C. elegans* let-7 micorRNA is transcriptionally controlled utilizing a temporal regulatory element in its promoter," *Developmental Biology* (2003) vol. 259, pp. 364-379.
Mansfield, Jennifer H., et al., "MicroRNA-responsive 'sensor' transgenes uncover Hox-like and other developmentally regulated patterns of vertebrate microRNA expression," *Nature Genetics* (2004) vol. 36:10, pp. 1079-1083.
Arts, G., et al., Adenoviral Vectors Expressing siRNAs for Discovery and Validation of Gene Function, Genome Research 2003, vol. 13, pp. 2325-2332.

(Continued)

*Primary Examiner* — J. E. Angell
(74) *Attorney, Agent, or Firm* — Steptoe & Johnson LLP

(57) ABSTRACT

A gene vector comprising a miRNA sequence target.

12 Claims, 10 Drawing Sheets

(56) References Cited

OTHER PUBLICATIONS

Barnes, D., et al., Harnessing Endogenous miRNAs to Control Virus Tissue Tropism as a Strategy for Developing Attenuated Virus Vaccines, Cell Host & Microbe, Sep. 11, 2008, vol. 4, pp. 239-248.
Brown, B.D., et al., A microRNA-regulated lentiviral vector mediates stable correction of hemophilia B mice, Blood, Dec. 15, 2007, vol. 110, No. 13, pp. 4144-4152.
Brown, B.D., et al., Endogenous microRNA can be broadly exploited to regulate transgene expression according to tissue, lineage and differentiation state. Nat Biotechnol. Dec. 2007; 25(12):1457-67. Epub Nov. 16, 2007.
Brown, B.D., et al., Exploiting and antagonizing microRNA regulation for therapeutic and experimental applications, Nature Reviews Genetics, Aug. 2009, vol. 10, pp. 578-584.
Cawood, R.. et al., Use of Tissue-Specific MicroRNA to Control Pathology of Wild-Type Adenovirus without Attenuation of Its Ability to Kill Cancer Cells, PLoS Pathogens May 2009, vol. 5, No. 5, e1000440.
Grimm, D,. et al., Therapeutic application of RNAi: is mRNA targeting finally ready for prime time?, The Journal of Clinical Investigation, Dec. 2007, vol. 117, No. 12, pp. 3633-3641.
He, L., et al., MicroRNAs: Small RNAs with a big role in gene regulation, Nature Reviews Genetics, Jul. 2004, vol. 5, pp. 522-531.
Kay, M.A., MicroRNAs outwit immune limitations in gene therapy, Blood, Dec. 15, 2007, vol. 110, No. 13, pp. 4136-4137.
Kay, M.A., State-of-the-art gene-base therapies: the road ahead, Nature Reviews Genetics, Apr. 6, 2011 (Advance Online publication).
Kelly, E.J., et al., Engineering microRNA responsiveness to decrease virus pathogenicity, Nature Medicine, Nov. 2008, vol. 14, No. 11, pp. 1278-1283.
Kelly, E.J., et al., MicroRNAs and the Regulation of Vector Tropism, Molecular Therapy, 2009, vol. 17, No. 3, pp. 409-416.
Kootstra, N.A., et al., Efficient Production of Human FVIII in Hemophilic Mice Using Lentiviral Vectors, Molecular Therapy, 2003, vol. 7, No. 5, pp. 623-631.
Marquez, R.T., et al., Advances in MicroRNAs: Implications for Gene Therapists, Human Gene Therapy, Jan. 2008, vol. 19, p. 27-37.
Mátrai, J., et al., Recent Advances in Lentiviral Vector Development and Applications, Molecular Therapy, Mar. 2010, vol. 18, No. 3, pp. 477-490.
Odom, G.L., et al., Viral-mediated gene therapy for the muscular dystrophies: Success, limitations and recent advances, Biochimica et Biophysica Acta, 2007, vol. 1772, pp. 243-262.
Perez, J.T., et al., Micro-RNA-mediated species-specific attenuation of influenza A virus, Nature Biotechnology, Jun. 2009, vol. 27, No. 6, pp. 572-578.
Pierce, G.F,. et al., Gene therapy, bioengineered clotting factors and novel technologies for haemophilia treatment, Journal of Thrombosis and Haemostasis, 2007, vol. 5, pp. 901-906.
Qasim, W., et al., RISC control for gene therapy, Nature Biotechnology, Jun. 2006, vol. 24, No. 6, pp. 661-662.
Xie, J., et al., MicroRNA-regulated, Systemically Delivered rAAV9: A Step Closer to CNS-restricted Transgene Expression, Mar. 2011, vol. 19, No. 3, pp. 526-535.
Japanese Office Action dated Nov. 26, 2015 issued in JP Application No. 2008-512952.
Extended European Search Report dated Jan. 18, 2016, issued in EP Application No. 15191665.7.
Annoni, A et al. (2013) EMBO Mol. Med. 5: 1684-1697.
Escobar, G. et al. (2014) OncoImmunology e28696.
Gentner, B. et al. (2010) Sci. Transl. Med. 2: 58ra84.
Chiriaco, M. et al. (2014) Mol. Ther. 22: 1472-1483.
Escobar, G. et al. (2014) Sci. Transl. Med. 6: 217ra3.
Mátrai, J. et al. (2011) Hepatology 53: 1696-1707.
McManus, et al., "Gene silencing in mammals by small interfering RNAs", Nature Reviews, Oct 2002, vol. 3, p. 737-747.

Mansfield, J. H., et al., "Micro-RNA-responsive 'sensor' transgenes uncover Hox-like and other developmentally regulated patters of vertebrate microRNA expression," Nat. Genetics (2004) vol. 36, pp. 1079-1083.
Lai, E.C., et al. "Pervasive regulation of Drosophila Notch target genes by GY-box-, Brd-box-, and K-box-class microRNAs," Genes Dev. (2005) vol. 19 pp. 1067-1080.
Gong, H., et al., "The Role of Small RNAs in Human Diseases: Potential Troublemaker and Therapeutics," Medic. Res. Rev. (2005) vol. 25, pp. 361-381.
Baek D et al., The impact of microRNAs on protein output, Nature, 2008, Sep. 4, 2008, vol. 455, No. 7209, p. 64-71.
Barad, O., Meiri, E., Avniel, A., Aharonov, R., Barzilai, A., Bentwich, I., Einav, U., Gilad, S., Hurban, P., Karov, Y., et al. (2004). MicroRNA expression detected by oligonucleotide microarrays: system establishment and expression profiling in human tissues. Genome Res 14, 2486-2494.
Bartel, D. P., and Chen, C. Z. (2004). Micromanagers of gene expression: the potentially widespread influence of metazoan microRNAs. Nat Rev Genet 5, 396-400.
Baskerville, S., and Bartel, D. P. (2005). Microarray profiling of microRNAs reveals frequent coexpression with neighboring miRNAs and host genes. Rna 11, 241-247.
Brennecke J, Stark A, Russell RB, Cohen SM, Principles of microRNA-target recognition, PLoS Biol., Mar. 2005, vol. 3, No. 3, e85.
Brown BD, Gentner B, Cantore A, Colleoni S, Amendola M, Zingale A, Baccarini A, Lazzari G, Galli C, Naldini L. Endogenous microRNA can be broadly exploited to regulate transgene expression according to tissue, lineage and differentiation state. Nat Biotechnol. Dec. 2007;25(12):1457-67. Epub Nov. 16, 2007.
Brown, B. D., and Lillicrap, D. (2002). Dangerous liaisons: the role of "danger" signals in the immune response to gene therapy. Blood 100, 1133-1140.
Brown, B. D., Shi, C. X., Powell, S., Hurlbut, D., Graham, F. L., and Lillicrap, D. (2004a). Helper-dependent adenoviral vectors mediate therapeutic factor Viii expression for several months with minimal accompanying toxicity in a canine model of severe hemophilia A. Blood 103, 804-810.
Brown, B. D., Shi, C. X., Rawle, F. E., Tinlin, S., McKinven, A., Hough, C., Graham, F. L., and Lillicrap, D. (2004b). Factors influencing therapeutic efficacy and the host immune response to helper-dependent adenoviral gene therapy in hemophilia A mice. J Thromb Haemost 2, 111-118.
Calin G.A. et al., Frequent deletions and down-regulation of microRNA genes miR15 and miR16 at 13q14 in chronic lymphocytic leukemia, Proc Natl Acad Sci (2002) 99:15524-15529.
Calin, G. A., Liu, C. G., Sevignani, C., Ferracin, M., Felli, N., Dumitru, C. D., Shimizu, M., Cimmino, A., Zupo, S., Dono, M., et al. (2004a). MicroRNA profiling reveals distinct signatures in B cell chronic lymphocytic leukemias. Proc Natl Acad Sci U S A 101, 11755-11760.
Calin, G. A., Sevignani, C., Dumitru, C. D., Hyslop, T., Noch, E., Yendamuri, S., Shimizu, M., Rattan, S., Bullrich, F., Negrini, M., and Croce, C. M. (2004b). Human microRNA genes are frequently located at fragile sites and genomic regions involved in cancers. Proc Natl Acad Sci U S A 101, 2999-3004.
De Geest, B. R., Van Linthout, S. A., and Collen, D. (2003). Humoral immune response in mice against a circulating antigen induced by adenoviral transfer is strictly dependent on expression in antigen-presenting cells. Blood 101, 2551-2556.
De Palma, M., Montini, E., de Sio, F. R., Benedicenti, F., Gentile, A., Medico, E., and Naldini, L. (2005). Promoter trapping reveals significant differences in integration site selection between MLV and HIV vectors in primary hematopoietic cells. Blood 105, 2307-2315.
Dobrzynski E, Mingozzi F, Liu YL, bendo E, Cao O, Wang L, Herzog RW, Induction of antigen-specific CD4+ T-cell anergy and eletion by in vivo viral gene transfer, Blood, Aug. 15, vol. 104, No. 4, p. 969-977. Epub Apr. 22, 2004.
Doench, J. G., Petersen, C. P., and Sharp, P. A. (2003). siRNAs can function as miRNAs. Genes Dev 17, 438-442.

(56) References Cited

OTHER PUBLICATIONS

Farh, K. K., Grimson, A., Jan, C., Lewis, B. P., Johnston, W. K., Lim, L. P., Burge, C. B., and Bartel, D. P. (2005). The widespread impact of mammalian MicroRNAs on mRNA repression and evolution. Science 310, 1817-1821.
Fischer A et al., Gene therapy of inherited diseases, Lancet, Jun. 14, 2008, vol. 371, p. 2044-2047.
Follenzi, A., Battaglia, M., Lombardo, A., Annoni, A., Roncarolo, M. G., and Naldini, L. (2004). Targeting lentiviral vector expression to hepatocytes limits transgene-specific immune response and establishes long-term expression of human antihemophilic factor IX in mice. Blood 103, 3700-3709.
Follenzi, A., Sabatino, G., Lombardo, A., Boccaccio, C., and Naldini, L. (2002). Efficient gene delivery and targeted expression to hepatocytes in vivo by improved lentiviral vectors. Hum Gene Ther 13, 243-260.
Gottwein E et al., Viral and cellular microRNAs as determinants of viral, Cell Host Microbe Jun. 12, 2008, vol. 3, No. 6, p. 375-387.
Griffiths-Jones, S., Grocock, R. J., van Dongen, S., Bateman, A., and Enright, A. J. (2006). miRBase: microRNA sequences, targets and gene nomenclature. Nucleic Acids Res 34, D140-144.
Houbaviy HB et al., Embryonic Cell-Specific MicroRNAs, Developmental Cell, 2003, 5, 351-358.
Huber B E et al., Retroviral-mediated gene therapy for the treatment of hepatocellular carcinoma: An innovative approach for cancer therapy, Proc. Natl. Acad. Sci. USA, 1991, vol. 88, p. 8039-8043.
Iorio, M. V., Ferracin, M., Liu, C. G., Veronese, A., Spizzo, R., Sabbioni, S., Magri, E., Pedriali, M., Fabbri, M., Campiglio, M., et al. (2005). MicroRNA gene expression deregulation in human breast cancer. Cancer Res 65, 7065-7070.
Kay M, State-of-the-art gene-based therapies: the road ahead, Nat Rev Genet May 2011, vol. 12, p. 316-328.
Krichevsky et al, A microRNA array reveals extensive regulation of microRNAs during brain development, RNA (2003), 9:1274-1281.
LoDuca P et al., Hepatic Gene Transfer as a Means of Tolerance Induction to Transgene Products, Curr Gene Ther, Apr. 2009, vol. 9, No. 2, p. 104-114.
Mansfield JH et al., MicroRNA-responsive "sensor" transgenes uncover Hox-like and other develomentally regulated patterns of vertebrate microRNA expression, Nature Genetics, 2004, 36(10):1079-83 Epub, erratum in Nat Genet (2004) 36(11):1238.
Mansfield, J. H., Harfe, B. D., Nissen, R., Obenauer, J., Srineel, J., Chaudhuri, A., Farzan-Kashani, R., Zuker, M., Pasquinelli, A. E., Ruvkun, G., et al. (2004). MicroRNA-responsive 'sensor' transgenes uncover Hox-like and other developmentally regulated patterns of vertebrate microRNA expression. Nat Genet 36, 1079-1083. Epub, erratum in Nat Genet (2004) 36(11):1238.
Metzler M et al, High Expression of Precursor MicroRNA-155/BIC RNA in Children with Burkitt Lymphoma, Genes Chromosomes Cancer (2004) 39:167-169.
Mingozzi, F., Liu, Y. L., Dobrzynski, E., Kaufhold, A., Liu, J. H., Wang, Y., Arruda, V. R., High, K. A., and Herzog, R. W. (2003). Induction of immune tolerance to coagulation factor Ix antigen by in vivo hepatic gene transfer. J Clin Invest 111, 1347-1356.
Mitta B et al.., Advanced modular self-inactivating lentiviral expression vectors for multigene interventions in mammalian cells and in vivo transduction, Nucleic Acids Research, 2002 vol. 30, n0. 21 e113, 1-18.
Pfeifer A et al., Transgenesis by lentivral vectors: lack of gene silencing in mammalian embryonic stem cells and preimplantation embryos, Proc. Natl. Acad. Sci., 2002, vol. 99, No. 4, p. 2140-2145.
Reinhart, B. J., Slack, F. J., Basson, M., Pasquinelli, A. E., Bettinger, J. C., Rougvie, A. E., Horvitz, H. R., and Ruvkun, G. (2000). The 21-nucleotide let-7 RNA regulates developmental timing in *Caenorhabditis elegans*. Nature 403, 901-906.
Robbins P D et al., Viral Vectors for Gene Therapy, Pharmacol Ther., 1998, vol. 80, No. 1, p. 35-47.
Saenz DT, Loewen N, Peretz M, Whitwam T, Barraza R, Howell KG, Holmes JM, Good M, Poeschla EM: Unintegrated lentivirus DNA persistence and accessibility to expressionin nondividing cells: Analysis with class I inegrase mutants, J Virol, 2004, vol. 78, No. 6, p. 2906-2920.
Sandrin, V., Russell, S. J., and Cosset, F. L. (2003). Targeting retroviral and lentiviral vectors. Curr Top Microbiol Immunol 281, 137-178.
Selbach M et al., Widespread changes in protein synthesis induced by microRNA, Nature, 2008, vol. 455, p. 58-63.
Sempere, L. F., Freemantle, S., Pitha-Rowe, I., Moss, E., Dmitrovsky, E., and Ambros, V. (2004). Expression profiling of mammalian microRNAs uncovers a subset of brain-expressed microRNAs with possible roles in murine and human neuronal differentiation. Genome Biol 5, R13.
Song J et al., Gene Silencing in Androgen-responsive prostate Cancer Cells from Tissue-Specific Prostate-Specific Antigen Promoter, Cancer Research, 2004, vol. 64, p. 7661-7663.
Stark A et al., Identification of *Drosophila* MicroRNA Targets, PloS Biol., Oct. 13, 2003, vol. 1, issue 3, p. 397-409.
Tenoever BR, RNA viruses and the host microRNA machinery, Nat Rev Microbiol Mar. 2013, vol. 11, p. 169-180.
Thomas, C. E., Ehrhardt, A., and Kay, M. A. (2003). Progress and problems with the use of viral vectors for gene therapy. Nat Rev Genet 4, 346-358.
Verma, I. M., and Weitzman, M. D. (2005). Gene Therapy: Twenty-First Century Medicine. Annu Rev Biochem 74, 711-738.
Yanez-Munoz RJ, Balaggan KS, MacNeil A, Howe SJ, Schmidt M, Smith AJ, Buch P, MacLaren RE, Anderson PN, Barker SE, Duran Y et al., Effective gene therapy with nonineegrating lentiviral vectors, Nat Med, 2006, nol. 12, No. 3, p. 348-353.
Zahler M H et al., The application of a lentiviral vector for gene transfer in fetal human hepatocytes, Journal of Gene Medicine, 2000, vol. 2, p. 186-193.
Zeng, Y., Wagner, E. J., and Cullen, B. R. (2002). Both natural and designed micro RNAs can inhibit the expression of cognate mRNAs when expressed in human cells. Mol Cell 9, 1327-1333.
Annoni, A. et al., EMBO Mol Med (2013) 5, 1684-1697.
Escobar et al., Sci Transl Med 6, 217ra3 (2014).
Chiriaco, M. et al., Mol Ther, Aug. 2014;22(8):1472-83.
Qiao et al, Gene Therapy (2011) 18, 403-410.
Sempere et al., Genome Biology 2004, 5:R13.
Geisler et al.,World J Exp Med, May 20, 2016; 6(2): 37-54.
Giraldez A J et al., MicroRNAs Regulate Brain Morphogenesis in Zebrafish, Science May 6, 2005, vol. 308 pp. 833-838.
Smirnova L et al., Regulation of miRNA expression during neural cell specification, Eur J Neurosci, Mar. 2005, vol. 21 pp. 1469-1477.
Cheng A M et al., Antisense inhibition of human miRNAs and indications for an involvement of miRNA in cell growth and apoptosis, Nucleic Acids Research, Mar. 2005 vol. 33, No. 4, p. 1290-1297.
Stöven S et al., Caspase-mediated processing of the *Drosophila* NF-κb factor Relish, Proc Natl Arad Sci USA, Mar. 2003, vol. 100, No. 17, pp. 9779-9784.

\* cited by examiner a.

A. Mature hsa-mir-142 stem loop sequence.

```
g         g  c           a         uaa ag a
  acagugca uca ccauaaaguag aagcacuac   c  c c
  ||||||||  |||  ||||||||||| |||||||||
  ugucaugu agu gguauuucauc uuugugaug   g  g u
g         g  a           c         -ug ga g
```

B. 1x.mir-142as.Target
TCCATAAAGTAGGAAACACTACA

SEQUENCE LISTING

```
<160> NUMBER OF SEQ ID NOS: 21

<210> SEQ ID NO 1
<211> LENGTH: 67
<212> TYPE: DNA
<213> ORGANISM: Artificial
<220> FEATURE:
<223> OTHER INFORMATION: Oligonucleotide

<400> SEQUENCE: 1
ctagagtcga ctccataaag taggaaacac tacacgattc cataaagtag gaaacactac      60
aaccggt                                                               67

<210> SEQ ID NO 2
<211> LENGTH: 57
<212> TYPE: DNA
<213> ORGANISM: Artificial
<220> FEATURE:
<223> OTHER INFORMATION: Oligonucleotide

<400> SEQUENCE: 2
tgtagtgttt cctactttat ggaatcgtgt agtgtttcct actttatgga gtcgact        57

<210> SEQ ID NO 3
<211> LENGTH: 51
<212> TYPE: DNA
<213> ORGANISM: Artificial
<220> FEATURE:
<223> OTHER INFORMATION: Oligonucleotide

<400> SEQUENCE: 3
tccataaagt aggaaacact acatcactcc ataaagtagg aaacactaca c              51

<210> SEQ ID NO 4
<211> LENGTH: 61
<212> TYPE: DNA
<213> ORGANISM: Artificial
<220> FEATURE:
<223> OTHER INFORMATION: Oligonucleotide

<400> SEQUENCE: 4
tcgagtgtag tgtttcctac tttatggagt gatgtagtgt ttcctacttt atggaaccgg      60
t                                                                     61
```

-continued

```
<210> SEQ ID NO 5
<211> LENGTH: 20
<212> TYPE: DNA
<213> ORGANISM: Artificial
<220> FEATURE:
<223> OTHER INFORMATION: Oligonucleotide primer

<400> SEQUENCE: 5
tgaaagcgaa agggaaacca                                                    20

<210> SEQ ID NO 6
<211> LENGTH: 15
<212> TYPE: DNA
<213> ORGANISM: Artificial
<220> FEATURE:
<223> OTHER INFORMATION: Oligonucleotide primer

<400> SEQUENCE: 6
ccgtgcgcgc ttcag                                                         15

<210> SEQ ID NO 7
<211> LENGTH: 18
<212> TYPE: DNA
<213> ORGANISM: Artificial
<220> FEATURE:
<223> OTHER INFORMATION: Oligonucleotide probe

<400> SEQUENCE: 7
ctctctcgac gcaggact                                                      18

<210> SEQ ID NO 8
<211> LENGTH: 20
<212> TYPE: DNA
<213> ORGANISM: Artificial
<220> FEATURE:
<223> OTHER INFORMATION: Oligonucleotide primer

<400> SEQUENCE: 8
agagggaaat cgtgcgtgac                                                    20

<210> SEQ ID NO 9
<211> LENGTH: 21
<212> TYPE: DNA
<213> ORGANISM: Artificial
<220> FEATURE:
<223> OTHER INFORMATION: Oligonucleotide primer

<400> SEQUENCE: 9
caatagtgat gacctggccg t                                                  21

<210> SEQ ID NO 10
<211> LENGTH: 23
<212> TYPE: DNA
<213> ORGANISM: Artificial
<220> FEATURE:
<223> OTHER INFORMATION: Oligonucleotide probe

<400> SEQUENCE: 10
cactgccgca tcctcttcct ccc                                                23

<210> SEQ ID NO 11
<211> LENGTH: 18
<212> TYPE: DNA
<213> ORGANISM: Artificial
<220> FEATURE:
<223> OTHER INFORMATION: Oligonucleotide primer
```

```
<400> SEQUENCE: 11
ggcacacgtg gcttttcg                                              18

<210> SEQ ID NO 12
<211> LENGTH: 24
<212> TYPE: DNA
<213> ORGANISM: Artificial
<220> FEATURE:
<223> OTHER INFORMATION: Oligonucleotide primer

<400> SEQUENCE: 12
ggtgaacctc gtaagtttat gcaa                                       24

<210> SEQ ID NO 13
<211> LENGTH: 24
<212> TYPE: DNA
<213> ORGANISM: Artificial
<220> FEATURE:
<223> OTHER INFORMATION: Oligonucleotide probe

<400> SEQUENCE: 13
tcaggacgtc gagtggacac ggtg                                       24

<210> SEQ ID NO 14
<211> LENGTH: 17
<212> TYPE: DNA
<213> ORGANISM: Artificial
<220> FEATURE:
<223> OTHER INFORMATION: Oligonucleotide primer

<400> SEQUENCE: 14
cagctcgccg accacta                                               17

<210> SEQ ID NO 15
<211> LENGTH: 14
<212> TYPE: DNA
<213> ORGANISM: Artificial
<220> FEATURE:
<223> OTHER INFORMATION: Oligonucleotide primer

<400> SEQUENCE: 15
gggccgtcgc cgat                                                  14

<210> SEQ ID NO 16
<211> LENGTH: 16
<212> TYPE: DNA
<213> ORGANISM: Artificial
<220> FEATURE:
<223> OTHER INFORMATION: Oligonucleotide probe

<400> SEQUENCE: 16
ccagcagaac acccccc                                               16

<210> SEQ ID NO 17
<211> LENGTH: 21
<212> TYPE: DNA
<213> ORGANISM: Artificial
<220> FEATURE:
<223> OTHER INFORMATION: Oligonucleotide primer

<400> SEQUENCE: 17
accacagtcc atgccatcac t                                          21
```

```
<210> SEQ ID NO 18
<211> LENGTH: 19
<212> TYPE: DNA
<213> ORGANISM: Artificial
<220> FEATURE:
<223> OTHER INFORMATION: Oligonucleotide primer

<400> SEQUENCE: 18
ggccatcacg ccacagstt                                                19

<210> SEQ ID NO 19
<211> LENGTH: 24
<212> TYPE: DNA
<213> ORGANISM: Artificial
<220> FEATURE:
<223> OTHER INFORMATION: Oligonucleotide probe

<400> SEQUENCE: 19
ccacccagaa gactgtggat ggcc                                          24

<210> SEQ ID NO 20
<211> LENGTH: 87
<212> TYPE: RNA
<213> ORGANISM: Mus musculus
<220> FEATURE:
<221> NAME/KEY: stem_loop
<222> LOCATION: (1)..(87)

<400> SEQUENCE: 20
gacagugcag ucacccauaa aguagaaagc acuacuaaca gcacuggagg guguaguguu   60
uccuacuuua uggaugagug uacugug                                       87

<210> SEQ ID NO 21
<211> LENGTH: 23
<212> TYPE: DNA
<213> ORGANISM: Artificial
<220> FEATURE:
<223> OTHER INFORMATION: miR-142 target sequence

<400> SEQUENCE: 21
tccataaagt aggaaacact aca                                           23
```

GENE VECTOR

CLAIM OF PRIORITY

This application claims priority under 35 USC 371 to International Application No. PCT/IB2006/002266, filed on May 26, 2006, which claims priority to U.S. Provisional Patent Application Ser. No. 60/684,954, filed May 27, 2005, each of which is incorporated by reference in its entirety.

FIELD OF THE INVENTION

The present invention relates to gene vectors for use in gene transfer and therapy applications, and to methods of producing them, and uses thereof.

BACKGROUND TO THE INVENTION

Lentiviral vectors (LVs) and other viral vectors are an attractive tool for gene therapy (Thomas et al., 2003). LVs can transduce a broad range of tissues, including nondividing cells such as hepatocytes, neurons and hematopoietic stem cells. Moreover, LVs integrate into target cell genomes and provide long-term transgene expression.

Although LVs can provide efficient and stable gene transfer, targeting expression to, or de-targeting expression from, a specific cell type remains difficult. This problem is particularly relevant following in vivo vector administration in which transgene expression may only be desired in a specific cell population, such as tumor cells or hepatocytes, but a broad spectrum of cell types are transduced. De-targeting expression is also important when progenitor or stem cells are transduced, but it is necessary to have transgene expression restricted to only one particular lineage of the differentiated population. To date, most efforts to address this problem have relied on either targeting the vector envelope or engineering tissue-specific promoters. There are, however, limitations with both these methods.

Targeted envelopes can reduce the vector titer and result in decreased vector infectivity (Sandrin et al., 2003). Tissue-specific promoters, which are constructed based on, but not identical to, naturally occuring promoter/enhancer elements, are often weakly expressed in target tissues compared to ubiquitously expressed promoters. In addition, these tissue-specific promoters do not always achieve absolute cell specificity (Follenzi et al., 2002). Transgene expression in non-target cells can occur for a variety of reasons, including 'leaky' promoter activity and promoter/enhancer trapping (De Palma et al., 2005). The trapping phenomenon comes about because the vector preferentially integrates at sites of active transcription, which can, in turn, drive transgene transcription independent of the vector's promoter.

In order to circumvent these problems and create a vector that can maintain high infectivity and robust expression, while enabling tight restriction of transgene expression from particular cell types, we developed a vector that is regulated by endogenously expressed microRNA (miRNA).

WO03/020931 describes an reporter system assay system displaying miRNA provides a method for measuring knockdown of a readily assayed gene. The system is used to determine if siRNAs and chimeric RNAs can decrease expression of the readily assayed luciferase gene.

US Patent Application 20050266552 describes the construction of a reporter construct suitable for introduction into mammalian cells to create cell lines that can be used for identification of genes involved in miRNA translational repression pathways and/or chemical modulators of such pathways.

Mansfield J H et al (2004) Nat Genet 36(10):1079-83 Epub, erratum in Nat Genet (2004) 36(11):1238; and Brennecke J et al (2005) PloS Biol 3(3):e85 both describe plasmids containing a reporter gene with miRNA target sequences. In both reports, the constructs were designed to monitor expression of endogenous miRNAs and not for the purpose of regulating a transgene and/or restricting expression to particular cell types.

An important feature of our invention that should be highlighted is that we describe how vectors can be designed to be regulated by endogenous miRNAs for controlling transgene expression to achieve specific expression profiles of the vector. Although reports already exist, which demonstrate that miRNA target sequences can be included in a reporter construct (a plasmid expressing a marker gene such as luciferase) to track expression of a miRNA, they do not describe exploiting miRNAs specifically for vector regulation. They particularly do not describe the use of the vectors of the present invention for gene therapy approaches to prevent immune mediated rejection of a transgene of interest or manufacturing approaches to increase titer of viral particles that express toxic genes which are normally toxic to the cell in which the viral particle is produced.

Statements of the Invention

According to one aspect of the present invention there is provided a gene transfer vector suitable for genetic engineering approaches, such as gene therapy, gene transfer and/or regulation of expression of a transgene comprising a miRNA sequence target. The miRNA is "operably linked" to the transgene. The term "operably linked" means that the components described are in a relationship permitting them to function in their intended manner.

In one embodiment the vector is a viral vector particle comprising a miRNA sequence target.

In one embodiment the particle comprises the genome (DNA or RNA) of the vector particle, which genome comprises the miRNA sequence target.

In one embodiment the particle comprises the genome of the vector particle, which RNA genome comprises the miRNA sequence target.

In one embodiment the particle comprises the RNA genome of the vector particle which RNA genome comprises multiple miRNA sequence targets, which may be in tandem.

In one embodiment the particle comprises the RNA genome of the vector particle which RNA genome comprises multiple different miRNA sequence target, which may be in tandem.

More then one copy of a miRNA target sequence included in the vector may increase the effectiveness of the system. Also that we envision that different miRNA target sequences could be included. For example, vectors which express more than one transgene may have the transgene under control of more than one miRNA target sequence, which may or may not be different. The miRNA target sequences may be in tandem, but other arrangements are envisaged, such the use of antisense orientations. Antisense orientations may be useful in the production of viral particles to avoid expression of gene products which may otherwise be toxic to the producer cells.

In another embodiment the particle comprises the genome of the vector particle, which RNA genome comprises a transgene.

Preferably the particle is derivable from a lentivirus.

In another embodiment the gene transfer vector is in the form of a non-viral gene transfer vector. In this embodiment, the gene transfer vector may comprise, or be in the form of, an expression vector or plasmid which comprises the miRNA target sequence and optionally a transgene.

Expression vectors as described herein comprise regions of nucleic acid containing sequences capable of being transcribed. Thus, sequences encoding mRNA, tRNA and rRNA are included within this definition.

The gene vector or gene transfer vector of the present invention may be used to deliver a transgene to a site or cell of interest. The vector of the present invention may be delivered to a target site by a viral or non-viral vector.

A vector is a tool that allows or facilitates the transfer of an entity from one environment to another. By way of example, some vectors used in recombinant DNA techniques allow entities, such as a segment of DNA (such as a heterologous DNA segment, such as a heterologous cDNA segment), to be transferred into a target cell. Optionally, once within the target cell, the vector may then serve to maintain the heterologous DNA within the cell or may act as a unit of DNA replication. Examples of vectors used in recombinant DNA techniques include plasmids, chromosomes, artificial chromosomes or viruses.

Non-viral delivery systems include but are not limited to DNA transfection methods. Here, transfection includes a process using a non-viral vector to deliver a gene to a target mammalian cell.

Typical transfection methods include electroporation, DNA biolistics, lipid-mediated transfection, compacted DNA-mediated transfection, liposomes, immunoliposomes, lipofectin, cationic agent-mediated, cationic facial amphiphiles (CFAs) (Nature Biotechnology 1996 14; 556), and combinations thereof.

Viral delivery systems include but are not limited to adenovirus vector, an adeno-associated viral (AAV) vector, a herpes viral vector, retroviral vector, lentiviral vector, baculoviral vector. Other examples of vectors include ex vivo delivery systems, which include but are not limited to DNA transfection methods such as electroporation, DNA biolistics, lipid-mediated transfection, compacted DNA-mediated transfection.

The term "vector particle" refers to the packaged retroviral vector, that is preferably capable of binding to and entering target cells. The components of the particle, as already discussed for the vector, may be modified with respect to the wild type retrovirus. For example, the Env proteins in the proteinaceous coat of the particle may be genetically modified in order to alter their targeting specificity or achieve some other desired function.

Preferably, the viral vector preferentially transduces a certain cell type or cell types.

More preferably, the viral vector is a targeted vector, that is it has a tissue tropism which is altered compared to the native virus, so that the vector is targeted to particular cells.

In another embodiment the particle comprising the miRNA target sequence is one targeted by mir-142as (also called hsa-mir-142-3p), let-7a, mir-15a, mir-16, mir-17-5p, mir-19, mir-142-5p, mir-145, mir-218 miRNA.

According to another aspect of the present invention there is provided a set of DNA constructs for producing the viral vector particle comprising a DNA construct encoding a packagable vector genome comprising a miRNA sequence target, and optionally a transgene. By packagable vector genome we mean that the vector genome is in an environment where it can be packaged into a viral vector particle. This generally requires the present of Gag-Pol and Env.

According to another aspect of the present invention there is provided a process for preparing a viral vector particle comprising introducing the set of DNA constructs of claim into a host cell, and obtaining the viral vector particle.

According to another aspect of the present invention there is provided a viral vector particle produced by the process of the present invention.

According to another aspect of the present invention there is provided a pharmaceutical composition comprising the gene vector or vector particle according to the present invention together with a pharmaceutically acceptable diluent, excipient or carrier.

According to a further aspect of the present invention there is provided a cell infected or transduced with the vector particle of the present invention. In one embodiment the cell comprises the corresponding miRNA. The cell may be transduced or infected in an in vivo or in vitro scenario. The cell may be derived from or form part of an animal, preferably a mammal, such as a human or mouse. Thus it will be appreciated that the present invention is useful in providing transgenic animals e.g., for use as disease models. In one embodiment, the mammal is a non-human mammal.

Current vector transcription control approaches mostly rely on the delivery of enhancer-promoter elements taken from endogenous genes (Thomas et al., 2003; Verma and Weitzman, 2005). Using these approaches, reconstitution of highly specific gene expression patterns, as often required for gene transfer and therapy applications, is limited by the delivery system, the vector capacity, and the positional effects of insertion (for integrating vectors). By developing new vectors which take advantage of endogenously expressed miRNAs for their regulation, the inventors have added a layer of control to the vectors that did not previously exist. This new approach allows specific repression of gene expression in selected cell types and lineages.

With this system we can reach much more stringent control of transgene expression than is currently possible with existing technologies.

When applied to integrating vectors, it can circumvent problems of transgene dysregulation, which can occur as a result of insertional position effects (integration next to strong promoter/enhancer sequences that override the transcriptional control of the vector-internal promoter) and enable highly cell-specific patterns of transgene expression.

Some Further Key Advantages of the Invention

Vectors, such as viral including lentiviral vectors, for transgene expression for gene transfer and therapy can be engineered with miRNAs target sequence in order to be recognized by endogenous miRNAs cell type specific, thus regulating transgene expression in a subset of cells. Moreover, combinations of miRNA target sequences can be used to obtain vectors with highly specific cell expression patterns.

The inventors demonstrate this with 9 different miRNAs, including let-7a, mir-15a, mir-16, mir-17-5p, mir-19, mir-142-3p, mir-142-5p, mir-145, and mir-218. They show that the concentration of a miRNA within a cell can be used to predict the expression profile of a vector. Thus, the method described by this patent provides a simple method for designing vectors with highly specific cell expression patterns.

A variety of uses for this invention can be envisioned.

Indeed, as an example, the inventors have demonstrated that transgene expression from a ubiquitously expressed promoter can be prevented precisely in a hematopoietic cell line by using a vector that displays the mir-142-3p target sequence in the transgene's 3'UTR, as shown in the figure below, because miR-142-3p has a cell-type specific expression pattern in hematopoietic tissues. Thus, this system does not reduce transgene expression in other cell types.

The inventors also demonstrate that incorporating a target sequence for mir-19a into the vector, transgene expression can be suppressed in 293T producer cells, which express mir-19a to high levels, and that this does not negatively effect the production of the vector. This strategy provides an important, and hitherto unavailable, means of producing high titer vectors which carry a toxic transgene.

A further usage of our invention is in the design of a vector system that expresses two transgenes with distinct expression profiles. The inventors demonstrate this by incorporating a target sequence for mir-142-3p into one of the two genes of a bidirectional lentiviral vector. In kidney cells both transgenes are expressed because mir-142-3p is not present. However, in hematopoietic cells, only one of the two transgenes is expressed. This construct provides proof-of-principle that miRNA regulation can be used to divergently regulated two transgenes from a single vector construct. Uses of this vector design include situations where a heterogeneous population of cells will be transduced, and expression of gene 1 is required in one of the cell types present, and expression of gene 2 is required in another cell type. This design could be used for therapeutic applications requiring both negative and positive selection of particular cells. For example, embryonic stem cells may be transduced by a single vector where gene 1 is a toxic transgene and gene 2 is a transgene that provides growth advantage to the cells. Gene 1 would contain a miRNA target sequence specific for neurons and gene 2 would contain a miRNA target sequence specific for embryonic stem cells. In this way, transduced embryonic stem cells can be directed to differentiated into neurons, and any cells which do not differentiate, and remain as undifferentiated embryonic stem cells would be selectively killed.

The inventors show that transfer of a miRNA target sequence into a cell, even at high copy, does not perturb the natural activity or expression of the endogenous miRNA, which is targeting the vector sequence.

We can also add combinations of miRNA target sequences to obtain vectors with highly specific cell expression patterns.

The miRNA-mediated approach for restricting gene expression has several advantages over other strategies of regulating transgenes. To date, most efforts to limit expression from professional antigen presenting cells (APCs) rely on tissue-specific promoters (Brown et al., 2004b; Follenzi et al., 2004; Mingozzi et al., 2003). Although this approach can successfully limit expression to target cells, 'leaky' expression in a fraction of non-target cells is observed. This occurs because the reconstituted promoter, modified for inclusion into a vector system, often loses some of its cell specificity and also because vector integration near active promoters and enhancers can activate the tissue-specific promoter and drive transgene expression. Because miRNA-mediated silencing occurs at the post-transcriptional level, promoter and enhancer trapping is irrelevant. As such, miRNA-regulation can be used to effectively de-target transgene expression from a particular cell type, while still allowing for broad tissue expression, as we have described here. miRNA regulation may also be used as a complimentary approach to regulating a transgene by promoter/enhancers. By including the miRNA target sequence in expression cassettes already under the control of a tissue-specific promoter, we add an additional layer of regulation which will eliminate off-target expression.

As a proof-of-principle that miRNA can be used to de-target transgene expression from particular cell types, we developed an LV which can provide robust expression in hepatocytes and other non-hematopoietic cells, while preventing expression from hematopoietic cells. This design is particularly relevant for systemic gene therapy in which the host immune response against the transgene limits therapeutic efficacy (Brown and Lillicrap, 2002). Studies from our laboratory and others indicate that a major factor contributing to the induction of a transgene-specific immune response following gene transfer is related to the site of transgene expression (Brown et al., 2004b; Follenzi et al., 2004). Vectors that are expressed in APCs of the hematopoietic system, such as macrophages and dendritic cells, are known to effectively trigger anti-transgene immune responses (De Geest et al., 2003).

Indeed, systemic administration of LV, expressing a transgene under the control of the CMV promoter, led to a high incidence of transgene expression in APCs of the liver and spleen, and this resulted in immune-mediated clearance of cells expressing the transgene (Follenzi et al., 2004). In contrast, when the CMV promoter was substituted with the liver-specific albumin promoter there was a reduction in the frequency and strength of the immune response. Although the incidence of immunity was reduced by the use of the albumin promoter, some level of immune responses were still observed. This was likely due to low level transgene expression in APCs from the albumin promoter, a result of leaky transcriptional activity and promoter/enhancer trapping. Thus, the problem of transgene expression in non-target cells, which is caused by events occurring at the level of transcriptional regulation, may be overcome by utilizing the miRNA system of gene regulation that acts post-transcriptionally. Restricting transgene expression to a particular cell type may also decrease the potential efficacy of gene transfer by limiting the pool of cells expressing the transgene.

Thus, we hypothesized that miRNA regulation, which de-targets rather than targets gene expression and functions at the post-transcriptional level, may provide a unique means for overcoming the limitations of current gene delivery systems. By preventing transgene expression in hematopoietic lineages, while permitting high levels of expression in non-hematopoietic cells, we reasoned that miRNA regulation could enable strong and stable gene transfer in the absence of an immune response.

We modified a pre-existing LV, containing the green fluorescent protein (GFP) reporter under transcriptional control of the ubiquitously expressed PGK promoter, to include the target sequence of a miRNA known to be expressed in cells of hematopoietic origin. Following systemic vector administration of our miRNA-regulated LV, gene expression was detected almost exclusively in hepatocytes and endothelial cells of the liver. Expression in Kupffer cells, liver-resident macrophages, was virtually undetectable. These results were in sharp contrast to administration of an LV that did not contain the miRNA target sequence, in which the majority of transgene expression occurred in Kupffer cells.

In a subsequent experiment, in which the vectors were injected into immunocompetent Balb/c mice, by two weeks post-injection we observed no GFP positive cell within the liver of LV.PGK.GFP treated mice. In stark contrast, mice treated with LV.PGK.GFP.142-3pT had a significant frequency of GFP positive hepatocytes at 2 weeks following vector administration. Moreover, GFP expression was found to persist for over 120 days post-injection (the last time point analyzed). Similarly, the miRNA-regulation strategy was also effective for preventing an immune response to a circulating antigen. Specifically, we treated hemophilia B mice with a lentiviral vector expressing human Factor IX (hFIX), and found that when the mir-142-3pT sequence was included in the vector, hFIX expression remained stable, whereas in mice treated with a similar vector without the mir-142-3pT sequence, hFIX expression was not detected after 3 weeks post-injection.

These results provide the first demonstration that miRNA can be used to retarget expression of a viral vector, and result in a long-lasting treatment for a disease. They also provide evidence that miRNA-regulation of the vector can reduce the anti-transgene immune response. This miRNA-regulated LV, the first of its kind, will have important implications for liver-directed gene therapy, where gene expression within hematopoeitic cells can be detrimental to therapeutic objectives. This invention may therefore be employed to prevent immune-mediated rejection of the transferred gene.

Upon vector administration in vivo, the present invention will avoid vector expression in antigen presenting cells of the immune system, which are part of the hematopoietic system, and thereby prevent the initiation of an immune response against the transgene. Conceivably, when applied to a tissue-specific promoter which targets expression to hepatocytes, it would allow suppressing ectopic expression in a transduced APC. This would potentially solve a major hurdle and long-standing problem in gene transfer; namely, immune-mediated rejection of the transferred gene.

Further particular and preferred aspects of the present invention are set out in the accompanying independent and dependent claims. Features of the dependent claims may be combined with features of the independent claims as appropriate, and in combinations other than those explicitly set out in the claims.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis. A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

BRIEF DESCRIPTION OF THE FIGURES

The present invention will be described further, by way of example only, with reference to preferred embodiments thereof as illustrated in the accompanying drawings, in which:

FIG. 9A shows the mature hsa-mir-142 stem loop sequence (SEQ ID NO: 20).

FIG. 9B shows the sequence of the mir-142 as target (SEQ ID NO: 21).

MICRORNAS (MIRNAS)

Figure 1:
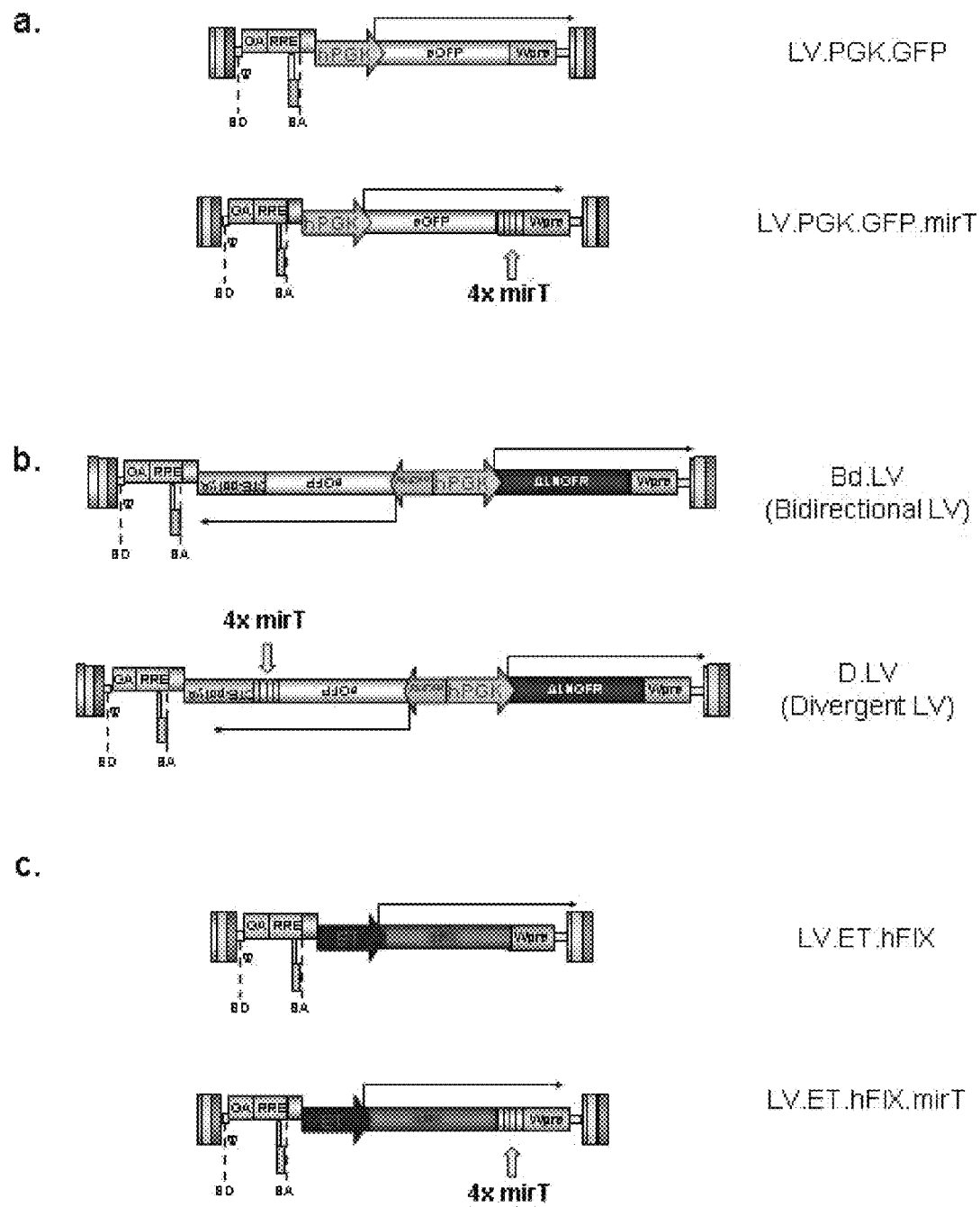
FIG. 1*a*. Schematic representation of a miRNA-regulated lentiviral vector system. Shown here is the parent lentiviral vector encoding enhanced green fluorescent protein (eGFP) under the transcriptional control of the ubiquitously expressed human PGK promoter (LV.PGK.GFP), and a modified vector, which contains 4 tandem copies of a sequence targeted by an endogenous miRNA (LV.PGK.GFP.mirT)
FIG. 1*b*. Schematic representation of a divergently regulated lentiviral vector system utilizing miRNA regulation. Shown here is the parent bidirectional lentiviral vector encoding eGFP and the mutated low-affinity nerve growth factor receptor (ΔLNGFR) under the transcriptional control of a bidirectional promoter construct (Bd.LV), which enables co-ordinate transcription of two transgenes as distinct transcripts. Bd.LVs were modified to include mirT sequences in the 3' untranslated region (3'UTR) of the eGFP expression cassette.
FIG. 1*c*. Schematic representation of a hepatocyte-specific, miRNA-regulated lentiviral vector system. Shown here is the parent lentiviral vector encoding human clotting factor IX (hFIX) under the transcriptional control of a synthetic liver-specific promoter/enhancer element. (LV.ET.hFIX), and a modified vector, which contains 4 tandem copies of a sequence targeted by an endogenous miRNA (LV.ET.hFIX.mirT)

miRNAs are small, RNA molecules encoded in the genomes of plants and animals. These highly conserved, ~21-mer RNAs regulate the expression of genes by binding to specific mRNAs (He and Hannon, 2004).

miRNAs are a family of small, non-coding RNAs that regulate gene expression in a sequence-specific manner.

In summary from microRNAs: SMALL RNAS WITH A BIG ROLE IN GENE REGULATION, Lin He & Gregory J. Hannon *Nature Reviews Genetics* 5, 522-531 (2004):

MicroRNAs (miRNAs) are a family of ~21-25-nucleotide small RNAs that negatively regulate gene expression at the post-transcriptional level.

The founding members of the miRNA family, lin-4 and let-7, were identified through genetic screens for defects in the temporal regulation of *Caenorhabditis elegans* larval development.

Owing to genome-wide cloning efforts, hundreds of miRNAs have now been identified in almost all metazoans, including flies, plants and mammals.

MiRNAs exhibit temporally and spatially regulated expression patterns during diverse developmental and physiological processes.

The majority of the animal miRNAs that have been characterized so far affect protein synthesis from their target mRNAs. On the other hand, most of the plant miRNAs studied so far direct the cleavage of their targets.

The degree of complementarity between a miRNA and its target, at least in part, determines the regulatory mechanism.

In animals, primary transcripts of miRNAs are processed sequentially by two RNase-III enzymes, Drosha and Dicer, into a small, imperfect dsRNA duplex (miRNA: miRNA*) that contains both the mature miRNA strand and its complementary strand (miRNA*). Relative instability at the 5' end of the mature miRNA leads to the asymmetric assembly of the mature miRNA into the effector complex, the RNA-induced silencing complex (RISC).

Ago proteins are a key component of the RISC. Multiple Ago homologues in various metazoan genomes indicate the existence of multiple RISCs that carry out related but specific biological functions.

Bioinformatic prediction of miRNA targets has provided an important tool to explore the functions of miRNAs.

Several hundred miRNAs have been cloned and sequenced from mouse, human, *Drosphila*, *C, elegans* and *Arabidopsis*. Examples of such sequences may be found on www.sanger.ac.uk (Griffiths-Jones et al., 2006). Further miRNA target sequences may be searched at www.miRNA.org.

Like mRNAs, miRNA expression profiles appear to vary from tissue to tissue but a similar for identical tissues in different individuals (Baskerville and Bartel, 2005). Determining an miRNA with the desired expression profile may be achieved using techniques known to those skilled in the art. Once, the miRNA has been identified the corresponding target sequence can readily be determined using, for example, the databases indicated above.

For example, the mirVana™ miTNA Probe Set and mirVana™ miTNA Labelling Kit available from Ambion, Inc. may be used to compare the miRNA expression profiles in human tissues according to the manufacturer's instructions.

Another common way of identifying tissue-specific miRNAs is using Northern Blot. An example of such a technique is described in Lagos-Quintana M et al, Current Biol (2002) 12:735-739 in which they identify 34 novel miRNAs by tissue-specific cloning of approximately 21-nucleotide RNAs from mouse (Lagos-Quintana et al., 2002).

Similarly, Michael M et al, Mol Can Res (2003) 1:882-891 describes the identification of 28 different miRNA sequences in colonic adenocarcinomas and normal mucosa.

Chen C-Z et al, Science (2004) 303:83-86 describes three miRNAs, miR-181, miR-142 and miR-223 which are specifically expressed in hematopoietic cells (Chen et al., 2004).

Sempere L et al, Genome Biology (2004) 5:R13 discloses a total of 17 miRNAs detected exclusively in a particular mouse organ; these included: seven brain-specific miRNAs (miR-9, -124a, -124b, -135, -153, -183, -219), six lung-specific miRNAs (miR-18, -19a, -24, -32, -130, -213), two spleen-specific miRNAs (miR-189, -212), one liver-specific miRNA (miR-122a), and one heart-specific miRNA (miR-208). All of the indicated mouse brain-, liver- and heart-specific miRNAs were also detected in the human counterpart organs (miRNA expression was not examined in human kidney, lung or spleen), with the exception of miR-183 in the human brain. Among the 75 miRNAs that were detected in two or more mouse organs, the levels of 14 of these were detected in a particular mouse organ at levels at least two-fold higher than in any other organ; these included: seven brain-enriched miRNAs (miR-9*, -125a, -125b, -128, -132, -137, -139), three skeletal muscle-enriched miRNAs (miR-1d, -133, -206), two kidney-enriched miRNAs (miR-30b, -30c), and one spleen-enriched miRNA (miR-99a). All brain-enriched and skeletal muscle-enriched miRNAs had similar elevated levels in the human counterpart organs. The high conservation of expression of these organ-specific and organ-enriched miRNAs between mouse and human suggests that they may play a conserved role in the establishment and/or maintenance of a cell or tissue type of that particular organ (Sempere et al., 2004).

Baskerville & Bartel, RNA (2005) 11:241-247 discloses a microarray profiling survey and the expression patterns of 175 human miRNAs across 24 different human organs. The results show that proximal pairs of miRNAs are generally coexpressed (Baskerville and Bartel, 2005). In addition, an abrupt transition in the correlation between pairs of expressed miRNAs occurs at a distance of 50 kb, implying that miRNAs separated by <50 kb typically derive from a common transcript. Some miRNAs are within the introns of host genes. Intronic miRNAs are usually coordinately expressed with their host gene mRNA, implying that they also generally derive from a common transcript, and that in situ analyses of host gene expression can be used to probe the spatial and temporal localization of intronic miRNAs.

Barad et al, Genome Research (2004) 14:2486-2494 establishes a miRNA-specific oligonucleotide microarray system that enables efficient analysis of the expression of the human miRNAs identified so far. It shows that the 60-mer oligonucleotide probes on the microarrays hybridize with labeled cRNA of miRNAs, but not with their precursor hairpin RNAs, derived from amplified, size-fractionated, total RNA of human origin. Signal intensity is related to the location of the miRNA sequences within the 60-mer probes, with location at the 5' region giving the highest signals, and at the 3' end, giving the lowest signals. Accordingly, 60-mer probes harboring one miRNA copy at the 5' end gave signals of similar intensity to probes containing two or three miRNA copies. Mismatch analysis shows that mutations within the miRNA sequence significantly reduce or eliminate the signal, suggesting that the observed signals faithfully reflect the abundance of matching miRNAs in the labeled cRNA. Expression profiling of 150 miRNAs in five human tissues and in HeLa cells revealed a good overall concordance with previously published results, but also with some differences. They present data on miRNA expression in thymus, testes, and placenta, and have identified miRNAs highly enriched in these tissues. Taken together, these results highlight the increased sensitivity of the DNA microarray over other methods for the detection and study of miRNAs, and the immense potential in applying such microarrays for the study of miRNAs in health and disease (Barad et al., 2004).

Kasashima K et al, Biochem Biophys Res Commun (2004) 322(2):403-10 describes the identification of three novel and 38 known miRNAs expressed in human leukemia cells (HL-60) (Kasashima et al., 2004).

Mansfield J et al, Nature Genetics (2004) 36:1079-1083 discloses the tissue-specific expression of several miRNAs during embryogenesis, including miR-10a and miR-196a (Mansfield et al., 2004).

Chen C-Z and Lodish H, Seminars in Immunology (2005) 17(2):155-165 discloses miR-181, a miRNA specifically expressed in B cells within mouse bone marrow (Chen and Lodish, 2005). It also discloses that some human miRNAs are linked to leukemias; the miR-15a/miR-16 locus is frequently deleted or down-regulated in patients with B cell chronic lymphocytic leukemia and miR-142 is at a translocation site found in a case of aggressive B cell leukemia. It is stated that these results indicate that miRNAs may be important regulators of mammalian hematopoiesis.

Methods of identifying new miRNAs and their target sequences using a computation approach are disclosed in WO2004/066183 and Brennecke J et al, PLoS Biology (2005) 3(3):0404-0418 (Brennecke et al., 2005).

The following table 1 summarises miRNA which may find applicability in the present invention.

TABLE 1

Expression studies on mammalian miRNAs

| Expression Pattern | miRNA | References |
|---|---|---|
| Tissue-specific expression patterns of mammalian miRNAs | | |
| ES-cell specific | miR-296 | a |
| Expressed in ES cells, but upregulated on differentiation | miR-21 and miR-22 | a |
| Expressed in both ES cells and various adult tissues | miR-15a, miR-16, miR-19b, miR-92, miR-93 miR-96, miR-130 and miR-130b | a |
| Enriched during mouse brain development | miR-128, miR-19b, miR-9, miR-125b, miR-131 miR-178, miR-124a, miR-266 and miR-103 | b, c |
| Enriched in adult brain | miR-9*, miR-125a, miR-125b, miR-128, miR-132 miR-137, miR-139, miR-7, miR-9, miR124a, miR-124b, miR-135, miR-153, miR-149, miR-183, miR-190, and miR-219 | b |
| Enriched in lung | miR-18, miR-19a, miR-24, miR-32, miR-130 miR-213, miR-20, miR-141, miR-193 and miR-200b | b |
| Enriched in spleen | miR99a, miR-127, miR-142-a, miR-142-s, miR-151, miR-189b and miR-212 | b |
| Haemetopoietic tissues | miR-181, miR-223 and miR-142 | b |
| Enriched in liver | miR-122a, miR-152, miR-194, miR-199 and miR-215 | b |
| Enriched in heart | miR-1b, miR-1d, miR-133, miR-206, miR-208 and miR-143 | b |
| Enriched in kidney | miR-30b, miR-30c, miR-18, miR-20, miR-24 miR-32, miR-141, miR-193 and miR-200b | b |
| Ubiquitously expressed | miR-16, miR-26a, miR-27a, miR-143a, miR-21 let-7a, miR-7b, miR-30b and miR-30c | b |
| Abnormal miRNA expression during tumorigenesis | | |
| Downregulated in chronic Lymphocytic leukaemias | miR-15 and miR-16 | d |
| Downregulated in lung cancer cell lines | miR-26a and miR-99a | e |
| Downregulated in colon Cancers | miR143/miR-145 cluster | f |

TABLE 1-continued

Expression studies on mammalian miRNAs

| Expression Pattern | miRNA | References |
|---|---|---|
| Upregulated in Burkitt Lymphoma | miR-155 | g |

ES cells, embryonic stem cells.

a - Houbaviy et al, Dev. Cell (2003) 5: 351-358.
b - Sempere et al, Genome Biol. (2004) 5, R13.
c - Krichevsky et al, RNA (2003), 9: 1274-1281.
d - Calin et al, Proc Natl Acad Sci (2002) 99: 15524-15529.
e - Calin et al, Proc Natl Acad Sci (2004) 101: 2999-3004.
f - Michael et al, Mol Cancer Res (2003) 1: 882-891.
g - Metzier et al, Genes Chromosomes Cancer (2004) 39: 167-169.

Although our data demonstrates the utility of this approach for restricting expression from hematopoeitic cells, the endogenous miRNA regulatory network will enable many more possibilities for tightly restricting transgene expression. Expression studies have already revealed miRNAs specific for many different cell types, including neurons, pancreatic islets, and adipose tissue. Using our design, a vector could be created which includes target sequences of miR-21 and miR-22, two miRNAs upregulated following embryonic stem cell (ESCs) differentiation (Houbaviy et al., 2003), tethered to a suicide gene such as thymidine kinase. This vector could serve to selectively kill undifferentiated ESCs in ESC-derived tissue, a much desired safety control for bringing ESC-based therapies to the clinic.

Another possible use of the miRNA-regulated vector design would be in the treatment of cancer. Several reports have indicated that specific miRNAs are downregulated in certain tumors. miR-15 and mir-45, for example, is down-regulated in chronic lymphocytic leukaemias and breast cancer (Calin et al., 2004a; Calin et al., 2004b; Iorio et al., 2005). The miR-15 or mir-145 target sequence could be included in a vector expressing a toxic transgene. Normal cells expressing miR-15 or mir-145, including vector producing cells, would suppress production of the toxin and thus survive, whereas transduced tumor cells, no longer expressing miR-15 or mir-145, would readily produce the toxin gene and die.

Another possible use of the miRNA-regulated vector design would be to prevent vector mobilization from transduced hematopoietic cells which become superinfected with wild-type virus. The miRNA target sequence could also be included in a region of the vector distinct from the expression cassette for the transgene.

The miRNA vector may be used in conjunction with a bidirectional promoter (Amendola et al., 2005). These vectors, which have the unique property that they produce two distinct mRNA transcripts from a single promoter, can be modified to include miRNA target sequences in one or both of the expression cassettes. Thus, addition of mir-142-3pT to transgene 1, but not transgene 2, would enable ubiquitous expression of transgene 2, while preventing expression of transgene 1 in hematopoeitic cells. This design will enable divergent regulation of two transgenes, a feat not possible with current technologies.

The miRNA may be used with a suitable gene vector, i.e. a vector suitable for delivering a gene (transgene) of interest, such as a viral vector. Examples of these are described below.

Retroviruses

During the past decade, gene therapy has been applied to the treatment of disease in hundreds of clinical trials. Various tools have been developed to deliver genes into human cells; among them, genetically engineered retroviruses, including lentiviruses, are currently amongst the most popular tool for gene delivery. Most of the systems contain vectors that are capable of accommodating genes of interest and helper cells that can provide the viral structural proteins and enzymes to allow for the generation of vector-containing infectious viral particles. Retroviridae is a family of retroviruses that differs in nucleotide and amino acid sequence, genome structure, pathogenicity, and host range. This diversity provides opportunities to use viruses with different biological characteristics to develop different therapeutic applications. As with any delivery tool, the efficiency, the ability to target certain tissue or cell type, the expression of the gene of interest, and the safety of retroviral-based systems are important for successful application of gene therapy. Significant efforts have been dedicated to these areas of research in recent years. Various modifications have been made to retroviral-based vectors and helper cells to alter gene expression, target delivery, improve viral titers, and increase safety. The present invention represents an improvement in this design process in that it acts to efficiently deliver genes of interest into such viral vectors.

Viruses are logical tools for gene delivery. They replicate inside cells and therefore have evolved mechanisms to enter the cells and use the cellular machinery to express their genes. The concept of virus-based gene delivery is to engineer the virus so that it can express the gene of interest. Depending on the specific application and the type of virus, most viral vectors contain mutations that hamper their ability to replicate freely as wild-type viruses in the host.

Viruses from several different families have been modified to generate viral vectors for gene delivery. These viruses include retroviruses, lentivirus, adenoviruses, adeno-associated viruses, herpes simplex viruses, picornaviruses, and alphaviruses. The present invention preferably employs retroviruses, including lentiviruses.

An ideal retroviral vector for gene delivery must be efficient, cell-specific, regulated, and safe. The efficiency of delivery is important because it can determine the efficacy of the therapy. Current efforts are aimed at achieving cell-type-specific infection and gene expression with retroviral vectors. In addition, retroviral vectors are being developed to regulate the expression of the gene of interest, since the therapy may require long-lasting or regulated expression. Safety is a major issue for viral gene delivery because most viruses are either pathogens or have a pathogenic potential. It is important that during gene delivery, the patient does not also inadvertently receive a pathogenic virus that has full replication potential.

Retroviruses are RNA viruses that replicate through an integrated DNA intermediate. Retroviral particles encapsidate two copies of the full-length viral RNA, each copy containing the complete genetic information needed for virus replication. Retroviruses possess a lipid envelope and use interactions between the virally encoded envelope protein that is embedded in the membrane and a cellular receptor to enter the host cells. Using the virally encoded enzyme reverse transcriptase, which is present in the virion, viral RNA is reverse transcribed into a DNA copy. This DNA copy is integrated into the host genome by integrase, another virally encoded enzyme. The integrated viral DNA is referred to as a provirus and becomes a permanent part of the host genome. The cellular transcriptional and translational machinery carries out expression of the viral genes. The host RNA polymerase II transcribes the provirus to generate RNA, and other cellular processes modify and transport the RNA out of the nucleus. A fraction of viral RNAs are spliced to allow expression of some genes whereas other viral RNAs remain full-length. The host translational machinery synthesizes and modifies the viral proteins. The newly synthesized viral proteins and the newly synthesized full-length viral RNAs are assembled together to form new viruses that bud out of the host cells.

Based on their genome structures, retroviruses can be classified into simple and complex retroviruses. Simple and complex retroviruses encode gag (group-specific antigen), pro (protease), pol (polymerase), and env (envelope) genes. In addition to these genes, complex retroviruses also encode several accessory genes.

Retroviruses can also be classified into oncoviruses, lentiviruses, and spumaviruses. Most oncoviruses are simple retroviruses. Lentiviruses, spumaviruses, and some oncoviruses are complex retroviruses. Currently, all three types of viruses are being exploited as gene therapy tools. Examples of each type will be discussed below.

Murine leukemia virus (MLV) is example of an oncovirus, human immunodeficiency virus 1 (HIV-1) is an example of a lentivirus, and human foamy virus is an example of a spumavirus.

When a replication-competent retrovirus infects a natural host cell, it can form a provirus in the host genome, express viral genes, and release new infectious particles to infect other hosts. In most gene therapy applications, it is not desirable to deliver a replication-competent virus into a patient because the virus may spread beyond the targeted tissue and cause adverse pathogenic effects. Therefore, in most retroviral systems designed for gene delivery, the viral components are divided into a vector and a helper construct to limit the ability of the virus to replicate freely.

The term vector generally refers to a modified virus that contains the gene(s) of interest (or transgene) and cis-acting elements needed for gene expression and replication. Most vectors contain a deletion(s) of some or all of the viral protein coding sequences so that they are not replication-competent. Helper constructs are designed to express viral genes lacking in the vectors and to support replication of the vectors. The helper function is most often provided in a helper cell format although it can also be provided as a helper virus or as cotransfected plasmids.

Helper cells are engineered culture cells expressing viral proteins needed to propagate retroviral vectors; this is generally achieved by transfecting plasmids expressing viral proteins into culture cells. Most helper cell lines are derived from cell clones to ensure uniformity in supporting retroviral vector replication. Helper viruses are not used often because of the likelihood that a replication-competent virus could be generated through high frequency recombination. Helper functions can also be provided by transient transfection of helper constructs to achieve rapid propagation of the retroviral vectors.

Most retroviral vectors are maintained as bacterial plasmids to facilitate the manipulation and propagation of the vector DNA. These double-stranded DNA vectors can be introduced into helper cells by conventional methods such as DNA transfection, lipofection, or electroporation. The helper cell shown expresses all of the viral proteins (Gag, Gag-Pol, and Env) but lacks RNA containing the packaging signal. Viral RNA is necessary for the formation and release of infectious viral particles, but it is not necessary for the formation of "empty" noninfectious viral particles. When the vector DNA is introduced into the helper cells, vector RNA containing a packaging signal is transcribed and efficiently packaged into viral particles. The viral particles contain viral proteins expressed from helper constructs and RNA transcribed from the vector. These viral particles can infect target cells, reverse transcribe the vector RNA to form a double-stranded DNA copy, and integrate the DNA copy into the host genome to form a provirus. This provirus encodes the gene(s) of interest and is expressed by the host cell machinery. However, because the vector does not express any viral proteins, it cannot generate infectious viral particles that can spread to other target cells.

Helper cells are designed to support the propagation of retroviral vectors. The viral proteins in the helper cells are expressed from helper constructs that are transfected into mammalian cells. Helper constructs vary in their mode of expression and in the genes they encode.

One-Genome Helper Constructs

In helper cell lines that were initially developed, all of the viral genes were expressed from one helper construct. Examples of these helper cells are C3A2 and -2. The helper constructs for these cell lines were cloned proviral DNAs that lacked the packaging signals. These helper cells can support efficient propagation of retroviral vectors. However, a major problem with these helper cells is that replication-competent viruses can be frequently generated during the propagation of the viral vector. The helper construct contains most of the viral genome and thus shares significant sequence homology with the retroviral vector. The sequence homology can facilitate recombination between the helper construct and the retroviral vector to generate replication-competent viruses. Although the helper RNA lacks the packaging signal, it can still be packaged into a virion with a low efficiency (approximately 100- to 1,000-fold less than RNAs containing). Retroviral recombination occurs frequently between the two copackaged viral RNAs to generate a DNA copy that contains genetic information from both parents. If the helper RNA and the vector RNA are packaged into the same virion, the large regions of sequence homology between the two RNAs can facilitate homologous recombination during reverse transcription to generate a replication-competent virus. A similar recombination event can also occur between the helper RNA and RNA derived from an endogenous virus at a lower efficiency to generate replication-competent viruses.

Split-Genome Helper Constructs

The safety concern associated with the generation of replication-competent viruses has provoked the design of many helper cell lines using "split genomes", including CRIP, GP+envAm12, and DSN. In these helper cells, the viral Gag/Gag-Pol polyproteins are expressed from one plasmid and the Env proteins are expressed from another plasmid. Furthermore, the two helper constructs also contain deletions of viral cis-acting elements to reduce or eliminate sequence homology with the retroviral vector. In these helper cells, genes encoding viral proteins are separated into two different constructs and the viral cis-acting elements are located in the vector. Therefore, several recombination events have to occur to reconstitute the viral genome. In addition, reducing the regions of homology decreases the probability that these recombination events will occur. Therefore, helper cells containing split-genome helper constructs are considered safer than helper cells containing one-genome helper constructs.

Inducible Helper Constructs

In contrast to the helper cell lines described above that express viral proteins constitutively, some helper cell lines have been designed to express the viral proteins in an inducible manner. One rationale for the generation of an inducible helper cell line is that some viral proteins are cytotoxic and cannot be easily expressed at high levels. By using an inducible system, expression of the cytotoxic proteins can be limited to the stage in which virus is propagated. By controlling the expression of the cytotoxic proteins, high viral titers can be achieved. Examples of the inducible helper cells include the 293GPG cells and HIV-1 helper cell lines.

Transient Transfection Systems

With the development of efficient transfection methods, transient transfection systems have also been developed for propagation of retroviral vectors. In these systems, helper functions are generally expressed from two different constructs, one expressing gag-pol and another expressing env. These two constructs generally share little sequence homology. The retroviral vector and the helper constructs are transfected into cells, and viruses are harvested a few days after transfection Systems That Generate Pseudotyped Viruses Pseudotyping refers to viral particles containing a viral genome from one virus and part (or all) of the viral proteins from a different virus. The most common form of pseudotyping involves one virus using the envelope protein of another virus. Some of the helper cell lines contain helper constructs that express gag-pol from one virus and env from another virus. Since the Gag polyproteins select the viral RNA, the viral vector to be propagated contains an RNA that is recognized by the Gag polyprotein expressed in these cells. However, the viral particles produced contain the Env protein derived from another virus. Therefore, these viral particles can only infect cells that express a receptor that can interact with the heterologous envelope protein. For example, the helper cell line PG13 expresses gag-pol from MLV and env from gibbon ape leukemia virus (GaLV). Because the PG13 cell line expresses MLV Gag polyprotein, it can efficiently package MLV-based retroviral vectors. It has also been shown that some envelopes derived from viruses of a different family can also pseudotype retroviruses and generate infectious viral particles. For example, the G protein of vesicular stomatitis virus (VSV), a rhabdovirus, can be used to generate pseudotyped retroviral vectors. These VSV G pseudotyped viruses exhibit a very broad host range and can infect a variety of cells that cannot normally be infected with retroviruses. Other envelopes that can be used for vector pseudotyping are those of the following viruses: the RD114 endogenous feline retrovirus, which effectively targets hematopoietic cells, the Lymphocytic ChorioMeningitis Virus (LCMV), the Rabies virus, the Ebola and Mokola viruses, the Ross River and Semliki Forest virus, and the baculovirus gp64 envelope.

Pseudotyping may involve for example a retroviral genome based on a lentivirus such as an HIV or equine infectious anaemia virus (EIAV) and the envelope protein may for example be the amphotropic envelope protein designated 4070A. Alternatively, envelope protein may be a protein from another virus such as an Influenza haemagglutinin. In another alternative, the envelope protein may be a modified envelope protein such as a mutant, truncated or engineered envelope protein (such as the engineered RD114 envelope). Modifications may be made or selected to introduce targeting ability or to reduce toxicity or for another purpose.

Systems Containing Genetically Modified env for Cell or Tissue Targeting

Interactions between the viral envelope proteins and the cellular receptors determine the host range of the virus. Strategies have been developed to target virus delivery into certain cell types by modifying the viral Env. After translation and modification, the SU portion of Env interacts with a cellular receptor. The modification of the SU portion of Env is often achieved by deletion of a part of the coding region for SU and replacing it with regions of other proteins. Proteins that have been used to modify the SU portion of Env include erythropoietin, heregulin, insulin-like growth factor I, and single-chain variable fragment antibodies against various proteins.

Hybrid Systems

Some recently developed systems use a hybrid approach for propagation of retroviral vectors. A helper cell line is used to constitutively express some of the viral proteins, whereas other viral proteins are introduced into the helper cell line by transient transfection. For example, a retroviral vector can be introduced into a helper cell line that constitutively expresses the MLV gag-pol. To propagate the retroviral vector, a plasmid designed to express the VSV G can be introduced into the system by transient transfection. As another variation on this theme, the retroviral vector itself may encode some of the viral proteins (for example, Gag/Gag-Pol), and a helper cell line may provide other viral proteins (Env) (Boerkoel et al., 1993). Approaches that use other viruses to deliver the retroviral helper constructs are also may used. For example, a modified herpes simplex virus was generated to contain the retroviral gag, pol, and env to serve the helper function. Similarly, adenovirus vectors and Semliki Forest virus-derived expression vectors have also been used to deliver genes encoding MLV viral proteins to helper cells.

Vectors Based on Different Retroviruses

Many retroviruses have been modified to generate vectors that can carry gene(s) of interest (transgene). Viral vectors generally contain all of the cis-acting elements needed for viral replication and gene expression. Additional elements may also be needed in vectors derived from some viruses to ensure successful gene delivery. The requirement for these cis-acting elements has often become apparent from greater understanding of the biology of these viruses. In addition, to allow easy manipulation in bacterial cells, most retroviral vectors are in plasmid form and have a backbone containing the bacterial origin of replication and an antibiotic resistance gene. The following steps are typically carried out to produce viral particles from retroviral vectors. Vector DNA is first introduced into the helper cells by transfection, electroporation, or lipofection. After introduction of the DNA into the helper cells, the vector DNA integrates into the helper cell and is expressed. The viral RNA is expressed from the 5'LTR and consists of all the sequences between the two R regions. This viral RNA contains the packaging signal and is packaged into the viral particles efficiently. During retroviral replication, the plasmid backbone sequences outside the two LTRs are not transferred to the target cells. The basic structures of some retroviral vectors derived from different retroviruses are described below.

Vectors Derived from Oncoviruses

Vectors derived from three different oncoviruses will be described here to represent some of the most widely used retroviral vectors. Oncoviruses can only infect dividing cells; therefore, vectors that are derived from oncoviruses can only be used to efficiently deliver genes into dividing cells. The requirement for cell proliferation can sometimes be used as an advantage to selectively target rapidly dividing cells (for example, cancer cells).

1. Murine Leukemia Virus-Based Vectors. Currently, MLV-based retroviral vectors and helper cells are the most frequently used system for gene delivery. The development and availability of engineered vectors and helper cell lines has promoted the popularity of MLV-based vectors. The vectors contain cis-acting viral sequences that are needed for gene expression and viral replication such as LTRs, PBS, PPT, and att. The packaging signal can be a minimum signal or a longer signal that extends into the gag open reading frame (+). When the + is present in the vector, it is necessary to mutate the translational initiation codon of gag to prevent expression of the truncated Gag protein. Several vectors have been designed to contain multiple restriction enzyme sites between the packaging signal and the 3' untranslated region. The presence of these cloning sites facilitates the construction of vectors that can express the gene of interest.

MLV-based vectors can be propagated in all of the MLV helper cell lines efficiently. There are several MLV envelope proteins that dictate the host range of MLV vectors. Viruses that use the ecotropic envelope can infect mouse cells but not cells derived from other species. Viruses that use the amphotropic envelope can infect both mouse cells and cells derived from other species, including human cells. Viruses that use the xenotropic envelope cannot infect mouse cells but can infect cells derived from other species. In addition, MLV vectors can also be propagated in spleen necrosis virus (SNV)-based helper cell lines. SNV is an avian virus that is distantly related to MLV. Surprisingly, SNV proteins retain the ability to interact with MLV cis-acting sequences and package MLV RNA, reverse transcribe the MLV genome, and integrate the MLV RNA into the host.

2. Spleen Necrosis Virus-Based Vectors. The required viral sequences in these vectors are very similar to those of the MLV vectors. The packaging signal of SNV, denoted E, does not extend into the gag open reading frame; therefore, most SNV-based vectors do not contain the gag coding regions. Similar to MLV vectors, the genes of interest are inserted into a linker region containing multiple restriction sites between the packaging signal and the 3' untranslated region. SNV-based vectors can be propagated in SNV-based helper cell lines such as C3A2, DSDH, DSH134G, and DSN.

3. Rous Sarcoma Virus- and Avian Leukosis Virus-Based Vectors. RSV is the only known acute oncogenic retrovirus that is replication-competent. In addition to gag-pol and env, RSV also encodes the oncogene v-src between env and the 3' LTR. A splice acceptor site upstream of the v-src allows the gene to be expressed as a spliced. RSV has the ability to code for an additional gene. Various modifications have been made to generate a replication-competent viral vector, an example of which is the replacement of v-src by a splice acceptor site and several restriction enzyme sites. DNA fragments can be inserted in the restriction sites to generate a replication-competent vector that expresses the gene of interest.

ALV has also been modified to generate vectors that require helper cells for their propagation. Similar to the MLV and SNV vectors described above, the basic structure of an ALV vector also contains the 5' and 3' LTRs, att, PBS, PPT, and a packaging signal. The packaging signal of ALV extends into the gag open reading frame, and the relevant portions of gag are included in ALV-based vectors to achieve efficient packaging.

Vectors Derived from Lentiviruses

In contrast to the oncoviruses, some lentiviruses have been shown to infect nondividing, quiescent cells. Lentiviruses are complex retroviruses that may need to express accessory proteins for regulation of their replication cycle. Some of these accessory proteins bind to regions of the viral genome to regulate gene expression. Therefore, lentivirus-based vectors need to incorporate additional cis-acting elements so that efficient viral replication and gene expression can occur. As examples of lentivirus-based vectors, HIV-1- and HIV-2-based vectors are described below.

The HIV-1 vector contains cis-acting elements that are also found in simple retroviruses. It has been shown that sequences that extend into the gag open reading frame are important for packaging of HIV-1. Therefore, HIV-1 vectors often contain the relevant portion of gag in which the translational initiation codon has been mutated. In addition, most HIV-1 vectors also contain a portion of the env gene that includes the RRE. Rev binds to RRE, which permits the transport of full-length or singly spliced mRNAs from the nucleus to the cytoplasm. In the absence of Rev and/or RRE, full-length HIV-1 RNAs accumulate in the nucleus. Alternatively, a constitutive transport element from certain simple retroviruses such as Mason-Pfizer monkey virus can be used to relieve the requirement for Rev and RRE. Efficient transcription from the HIV-1 LTR promoter requires the viral protein Tat. Therefore, it is important that Tat is expressed in target cells if efficient transcription from the HIV-1 LTR is needed. The need for Tat expression can be met by expressing the Tat gene from the retroviral vector. Alternatively, expressing the gene of interest from a heterologous internal promoter can circumvent the need for Tat expression.

Most HIV-2-based vectors are structurally very similar to HIV-1 vectors. Similar to HIV-1-based vectors, HIV-2 vectors also require RRE for efficient transport of the full-length or singly spliced viral RNAs.

It has also been demonstrated that the HIV-1 vector can be propagated to high viral titers using viral proteins from simian immunodeficiency virus. In one system, the vector and helper constructs are from two different viruses, and the reduced nucleotide homology may decrease the probability of recombination. In addition to vectors based on the primate lentiviruses, vectors based on feline immunodeficiency virus have also been developed as an alternative to vectors derived from the pathogenic HIV-1 genome. The structures of these vectors are also similar to the HIV-1 based vectors.

Vectors Derived from Spumaviruses

Foamy viruses are unconventional retroviruses in that many features in their replication cycle are different from those of oncoviruses and lentiviruses. Although these viruses can be toxic to cultured cells, none of the foamy viruses are known to cause any disease in hosts.

An example of a foamy virus vector contains the typical retroviral cis-acting sequences. In addition to the sequences in the 5' untranslated region, the 5' portion of the gag open reading frame and sequences in the 3' portion of the pol open reading frame are important for efficient packaging. Similar to the lentiviruses, expression from the human foamy virus promoter is activated by the viral protein Tas.

Design of Retroviral Vectors

Retroviral vectors may contain many different modifications that serve various purposes for the gene therapist. These modifications may be introduced to permit the expression of more than one gene, regulate gene expression, activate or inactivate the viral vectors, and eliminate viral sequences to avoid generation of a replication-competent virus. Some examples of these modifications are described below.

A. Standard Vectors

1. U3 Promoter-Driven Gene Expression. Full-length viral RNA is expressed from the retroviral promoter located in the U3 region of the 5' LTR. The viral RNA contains the R, U5, 5' untranslated region, a gene of interest, 3' untranslated region, U3, and R. The gene inserted between the 5' and 3' untranslated regions can be translated from the full-length RNA that is transcribed from the U3 promoter.

During the propagation of viral stocks, it is often desirable to express a selectable marker gene in the vector so that helper cells transfected or infected by the viral vectors can be selected. Therefore, it is often necessary to design retroviral vectors that express a selectable marker gene as well as a gene of interest. Drug resistance genes are frequently used as selectable markers, but other marker genes, such as the green fluorescent protein gene, can also be used to select for transfected or infected cells. The expression of two genes in a retroviral vector can be achieved by expressing the 3' gene by using an internal promoter, RNA splicing, or an internal ribosomal entry site (IRES).

2. Vectors That Use an Internal Promoter to Express Additional Genes. An example of gene expression from a retroviral vector containing an internal promoter where, e.g., the full-length RNA that is expressed from the viral U3 promoter is used to translate a first gene of interest(s). The subgenomic RNA that is expressed from the internal promoter is used to translate a second gene of interest(s).

3. Vectors That Use Splicing to Express Additional Genes. Retroviruses express env by regulated splicing. The splice donor site that is used to express env is located in the 5' untranslated region of retroviruses. During replication, some full-length viral RNAs are spliced to produce subgenomic viral RNAs that are used to express the Env proteins. Splicing vectors were developed by using the same principle to express two different genes by using the viral splice donor and splice acceptor sites. The advantage of splicing vectors is that only one promoter is necessary, and any potential for promoter interference is eliminated.

4. Vectors That Use Translational Control Signals to Express Additional Genes. It was first demonstrated in picornaviruses that sequences in the mRNA can serve as signals that allow the ribosome to bind to the middle of an mRNA and translate a gene far from the 5' end of the mRNA. These sequences (named IRES), are now commonly used in retroviral vectors. In addition to the IRES sequences identified in picornaviruses, IRES sequences have also been identified in the 5' untranslated regions of some retroviruses such as MLV, SNV, and an endogenous virus like particle (VL30). Therefore, it is also possible to use these retroviral IRES sequences to express a second gene. Other sequences allowing expression of multiple proteins from a single transcript are self-cleaving 2A-like peptides (also called CHYSEL, cis-acting hydrolase elements) derived from the Foot-and-Mouth disease virus and other picoRNA viruses. Alternatively bidirectional promoters can be used to express two genes from the same promoter.

B. Double-Copy Vectors

The fact that the LTR sequences are duplicated in retroviral vectors has been exploited to construct vectors containing two copies of the gene of interest. For example, the first set of double-copy vectors contains the gene of interest in the U3 region upstream of the viral. These genes are expressed using either an RNA polymerase II promoter or an RNA polymerase III promoter. This strategy has been shown to successfully increase the level of gene expression. In another example of a double-copy vector the vector contains the gene of interest in the middle of the R region.

C. Self-Inactivating Vectors

One safety concern associated with using retroviral vectors for gene therapy is that a replication-competent virus can be generated during propagation of the vectors, which can lead to inadvertent spread of the therapeutic vector to nontarget tissues. To address this concern, a class of vectors was designed to undergo self-inactivation. The principle is that after gene delivery, the vector will delete some of the cis-acting elements needed to complete another round of replication. Therefore, even in the presence of a replication-competent virus, these vectors cannot be transferred to other target cells efficiently. The generation of a replication-competent virus sometimes involves recombination between the defective helper plasmid and the vector encoding the gene of interest. Therefore, another possible benefit of the self-inactivating vector is that it may decrease the probability of generating a replication-competent virus.

1. U3 Minus Vectors. U3 minus vectors were the first self-inactivating retroviral vectors to be developed. These vectors are designed to delete the viral U3 promoter during reverse transcription so that the provirus in the target cell lacks a viral promoter. In these vectors, the U3 of the 5' LTR is intact, whereas the U3 of the 3' LTR is inactivated by a large deletion. The RNA generated from this vector contains R, U5, 5' untranslated region, gene(s) of interest, 3' untranslated region, a deleted U3, and R. During reverse transcription, the U3 at the 3' end of the viral RNA is normally used as a template to generate the LTR. Therefore, the viral DNA that is synthesized from the U3 minus vector through reverse transcription contains deleted U3 sequences in both LTRs. Since the viral promoter is deleted during reverse transcription, the gene of interest is under the control of an internal promoter. The advantage of the U3 minus vector is that it is potentially safer, since the probability of generation of a replication-competent virus is reduced. However, at a low frequency, recombination during DNA transfection can occur to regenerate the U3 at the 3' LTR. If this occurs, the resulting vector will still contain the promoter in the U3 and thus retain two complete LTRs. Additional modifications have been made in some U3 minus vectors to decrease the homology between the 5' and 3' LTRs, which reduces the probability of recombination and regeneration of an intact LTR during DNA transfection.

2. Cre/loxP Vectors. The Cre recombinase, a naturally occurring site-specific recombinase of bacteriophage P1, recognizes a 32-bp sequence named loxP. Cre can efficiently mediate site-specific recombination using two loxP sites separated by sequences of variable lengths. The recombination events include deletion, insertion, and inversion of the sequences between the loxP sites. This system has been exploited to develop self-inactivating retroviral vectors (Choulika et al., 1996; Russ et al., 1996). An example of such a vector contains an intact 5' LTR and all of the cis-acting elements needed for retroviral replication. The vector contains the cre recombinase gene that is expressed using an internal promoter. The 3' LTR has been modified by insertion of several sequences in the U3, including a loxP site, a promoter, and a gene of interest; in addition, the 3' U3 often contains a deletion to reduce the promoter activity. The full-length viral RNA is packaged into virion, and upon infection of target cells, the viral RNA is reverse-transcribed. The 3' U3 sequence is used as a template to synthesize both LTRs; consequently, the sequences in both LTRs contain a copy of the loxP site, a promoter, and a gene of interest. The cre gene is expressed, and the Cre recombinase is synthesized in the infected target cells. The Cre recombinase then mediates the deletion of sequences between the two loxP sites in the viral DNA, which results in deletion of the 5' LTR, the 5' untranslated region, the internal promoter, and cre. As a result, the provirus in the target cells contains only one LTR that expresses the gene of interest.

Using the same principle, the Cre/loxP system can be used to delete different sequences in the retroviral vector as well as delete portions of the helper construct in the packaging cells. Another application of the Cre/loxP system is that it can be used to delete the selectable marker from a retroviral vector after the viral DNA is integrated into the chromosome of the target cells. The selectable marker is included in the vector so that helper cells transfected with the vector DNA can be selected. Deletion of the selectable marker is desirable because the presence of the selectable marker can lead to promoter interference or an immune response against the transduced cells. Deletion of the selectable marker is accomplished by insertion of two loxP sites that flank the selectable marker gene. After the vector is introduced into target cells by infection, the target cells are infected with another vector that expresses the Cre recombinase. The Cre recombinase then deletes sequences between the two loxP sites, which include the selectable marker. As a result, the final provirus expresses only the gene of interest.

D. Self-Inactivating and Self-Activating Vectors

Depending on the properties and effects of the gene products, it may be desirable to have an inactivated gene of interest in the helper cells and activate this gene after it is delivered to target cells. For example, if the product from the gene of interest is cytotoxic, then expressing the gene in helper cells would result in toxicity and most likely reduce or eliminate viral production. A series of vectors have been generated to simultaneously activate a gene and inactivate the vector during gene delivery. This is accomplished by the frequent deletion of directly repeated sequences during reverse transcription. If directly repeated sequences are present in a virus, one copy of the direct repeat and all of the sequences between the two repeats can be deleted at high frequencies during reverse transcription. This property of reverse transcriptases has been exploited to generate the self-activating and self-inactivating retroviral vectors.

E. Vectors Targeted to Specific Cells

An important goal for gene therapists is to develop a means to target gene delivery to specific cell types or tissues. At least two strategies have been used in an effort to target gene delivery using retroviral vectors. One strategy is designed to control gene delivery at the point of virus entry into the host cell by using natural or genetically engineered envelope proteins that interact with cell-type-specific receptors. Another strategy is designed to control expression of the therapeutic gene in specific cell types by using tissue-specific promoters.

F. Vectors That Utilize Cell-Type-Specific Promoters

Promoters that are active in certain tissues or respond to certain reagents can be used to regulate the expression of a gene of interest. These promoters can be inserted between the LTRs of a retroviral vector. Alternatively, the regulated promoter can be used to replace the viral promoter in the U3 region. The design of a retroviral vector with an internal tissue-specific promoter is similar to that of other retroviral vectors containing internal promoters.

Virus Host Range

1. Considerations for Envelope Selection and Virus Host Range. The nature of the viral envelope protein determines whether a certain virus can enter a target cell. Therefore, it is important to consider whether the target cells have the correct cell surface receptor before the selection of an envelope protein that will be used for virus production (as discussed above).

The retroviral vector particle according to the invention will also be capable of transducing cells which are slowly-dividing, and which non-lentiviruses such as MLV would not be able to efficiently transduce. Slowly-dividing cells divide once in about every three to four days including certain tumour cells. Although tumours contain rapidly dividing cells, some tumour cells especially those in the centre of the tumour, divide infrequently. Alternatively the target cell may be a growth-arrested cell capable of undergoing cell division such as a cell in a central portion of a tumour mass or a stem cell such as a haematopoietic stem cell or a CD34-positive cell. As a further alternative, the target cell may be a precursor of a differentiated cell such as a monocyte precursor, a CD33-positive cell, or a myeloid precursor. As a further alternative, the target cell may be a differentiated cell such as a neuron, astrocyte, glial cell, microglial cell, macrophage, monocyte, epithelial cell, endothelial cell or hepatocyte. Target cells may be transduced either in vitro after isolation from a human individual or may be transduced directly in vivo.

Vectors Derived from Adenoviruses

The adenovirus is a double-stranded, linear DNA virus that does not go through an RNA intermediate. There are over 50 different human serotypes of adenovirus divided into 6 subgroups based on the genetic sequence homology all of which exhibit comparable genetic organisation. Human adenovirus group C serotypes 2 and 5 (with 95% sequence homology) are most commonly used in adenoviral vector systems and are normally associated with upper respiratory tract infections in the young.

The adenoviruses/adenoviral vectors of the invention may be of human or animal origin. As regards the adenoviruses of human origin, preferred adenoviruses are those classified in group C, in particular the adenoviruses of type 2 (Ad2), 5 (Ad5), 7 (Ad7) or 12 (Ad12). More preferably, it is an Ad2 or Ad5 adenovirus. Among the various adenoviruses of animal origin, canine adenovirus, mouse adenovirus or an avian adenovirus such as CELO virus (Cotton et al., 1993, J Virol 67:3777-3785) may be used. With respect to animal adenoviruses it is preferred to use adenoviruses of canine origin, and especially the strains of the CAV2 adenoviruses [manhattan strain or A26/61 (ATCC VR-800) for example]. Other adenoviruses of animal origin include those cited in application WO-A-94/26914 incorporated herein by reference.

As mentioned above, the organisation of the adenovirus genome is similar in all of the adenovirus groups and specific functions are generally positioned at identical locations for each serotype studied. The genome of adenoviruses comprises an inverted terminal repeat (ITR) at each end, an encapsidation sequence (Psi), early genes and late genes. The main early genes have been classified into an array of intermediate early (E1a), delayed early (E1b, E2a, E2b, E3 and E4), and intermediate regions. Among these, the genes contained in the E1 region in particular are necessary for viral propagation. The main late genes are contained in the L1 to L5 regions. The genome of the Ad5 adenovirus has been completely sequenced and is available on a database (see particularly Genbank Accession No. M73260). Likewise, parts, or even all of other adenoviral genomes (such as Ad2, Ad7, Ad12) have also been sequenced.

For use as recombinant vectors, an adenovirus is typically modified so as to make it incapable of replicating in an infected cell.

Thus, constructs described in the prior art include adenoviruses deleted for the E1 region, essential for viral replication, into which are inserted the heterologous DNA sequences (Levrero et al., 1991, Gene 101: 195; Gosh-Choudhury et al., 1986, Gene 50: 161). Moreover, to improve the properties of the vector, it has been proposed to create other deletions or modifications in the adenovirus genome. Thus, a heat-sensitive point mutation has been introduced into the ts125 mutant, making it possible to inactivate the 72 kDa DNA-binding protein (DBP). Preferably, a recombinant adenoviral vector used in the invention comprises a deletion in the E1 region of its genome. More particularly, it comprises a deletion in the E1a and E1b regions. According to a particularly preferred mode, the E1 region is inactivated by deletion of a PvuII-BglII fragment stretching from nucleotide 454 to nucleotide 3328, in the Ad5 adenovirus sequence (Genbank Accession No. M73260). In another preferred embodiment, the E1 region is inactivated by deletion of an HinfII-Sau3A fragment stretching from nucleotide 382 to nucleotide 3446.

Other adenoviral vectors comprise a deletion of another region essential for viral replication and/or propagation, the E4 region. The E4 region is involved in the regulation of the expression of the late genes, in the stability of the late nuclear RNAs, in decreasing host cell protein expression and in the efficiency of the replication of the viral DNA. Adenoviral vectors in which the E1 and E4 regions are deleted therefore possess very reduced viral gene expression and transcriptional background noise. Such vectors have been described for example in applications WO-A-94/28152, WO-A-95/02697, WO-A-96/22378. In addition, vectors carrying a modification of the IVa2 gene have also been described (WO-A-96/10088).

According to a preferred variant, a recombinant adenoviral vector used in the invention comprises, in addition, a deletion in the E4 region of its genome. More particularly, the deletion in the E4 region affects all the open reading frames. There may be mentioned, by way of a precise example, deletions of nucleotides 33466-35535 or 33093-35535. In particular, preferred vectors comprise a deletion of the whole of the E4 region. This may be carried deletion or excision of an MaeII-MscI fragment corresponding to nucleotides 35835-32720. Other types of deletions in the E4 region are described in applications WO-A-95/02697 and WO-A-96/22378, incorporated herein by reference.

Alternatively, only a functional part of E4 is deleted. This part comprises at least the ORF3 and ORF6 frames. By way of example, these coding frames can be deleted from the genome in the form of PvuII-AluI and BglII-PvuII fragments respectively, corresponding to nucleotides 34801-34329 and 34115-33126 respectively. The deletions of the E4 region of the virus Ad2 dl808 or of viruses Ad5 dl1004, Ad5 dl1007, Ad5 dl1011 or Ad5 dl1014 can also be used within the framework of the invention.

The positions given above refer to the wild-type Ad5 adenovirus sequence as published and accessible on a database. Although minor variations may exist between the various adenovirus serotypes, these positions are generally applicable to the construction of recombinant adenoviruses according to the invention from any serotype, and especially the adenoviruses Ad2 and Ad7.

Moreover, the adenoviruses produced may possess other alterations in their genome. In particular, other regions may be deleted to increase the capacity of the virus and reduce its side effects linked to the expression of viral genes. Thus, all or part of the E3 or IVa2 region in particular may be deleted. As regards the E3 region, it may however be particularly preferred to conserve the part encoding the gp19K protein. This protein indeed makes it possible to prevent the adenoviral vector from becoming the subject of an immune reaction which (i) would limit its action and (ii) could have undesirable side effects. According to a specific mode, the E3 region is deleted and the sequence encoding the gp19K protein is reintroduced under the control of a heterologous promoter.

The polynucleotide of the invention/NOI can be inserted into various sites of the recombinant genome. It can be inserted at into the E1, E3 or E4 region, as a replacement for the deleted or surplus sequences. It can also be inserted into any other site, outside the sequences necessary in cis for the production of the viruses (ITR sequences and encapsidation sequence).

The E2 region is essential as it encodes the 72 kDa DNA binding protein, DNA polymerase and the 80 kDa precurser of the 55 kDa Terminal Protein (TP) needed for protein priming to initiate DNA synthesis.

An alternative approach to making a more defective virus has been to "gut" the virus completely maintaining only the terminal repeats required for viral replication. The "gutted" or "gutless" viruses can be grown to high titres with a first generation helper virus in the 293 cell line.

The recombinant adenoviruses are typically produced in an encapsidation cell line, which is a cell line capable of complementing in trans one or more of the functions deficient in the recombinant adenoviral genome. One of these lines is for example line 293, into which part of the adenovirus genome has been integrated. More precisely, line 293 is a human kidney embryonic cell line containing the left end (about 11-12%) of the genome of serotype 5 adenovirus (Ad5), comprising the left ITR, the encapsidation region, the E1 region, including E1a and E1b, the region encoding protein pIX and part of the region encoding protein pIVa2. This line is capable of transcomplementing recombinant adenoviruses defective for the E1 region, that is to say lacking all or part of the E1 region, and of producing viral stocks having high titres. This line is also capable of producing, at a permissive temperature (32° C.), virus stocks comprising, in addition, the heat-sensitive E2 mutation.

Other cell lines capable of complementing the E1 region have been described, based in particular on human lung carcinoma cells A549 (WO-A-94/28152) or on human retinoblasts (Hum. Gen. Ther. (1996) 215). Moreover, cell lines capable of transcomplementing several adenovirus functions have also been described, for example cell lines complementing the E1 and E4 regions (Yeh et al., 1996, J. Virol. 70: 559; Krougliak et al., 1995, Hum. Gen. Ther. 6: 1575) and lines complementing the E1 and E2 regions (WO-A-94/28152, WO-A-95/02697, WO-A-95/27071).

The recombinant adenoviruses are usually produced by introducing the viral DNA into the encapsidation line, followed by lysis of the cells after about 2 or 3 days (the kinetics of the adenoviral cycle being 24 to 36 hours). For carrying out the process, the viral DNA introduced may be the complete recombinant viral genome, optionally constructed in a bacterium (WO-A-96/25506) or in a yeast (WO-A-95/03400), transfected into the cells. It may also be a recombinant virus used to infect the encapsidation line. The viral DNA may also be introduced in the form of fragments each carrying part of the recombinant viral genome and a region of homology which makes it possible, after introduction into the encapsidation cell, to reconstitute the recombinant viral genome by homologous recombination between the various fragments.

Replication-competent adenoviruses can also be used for gene therapy. For example, the E1a gene can be inserted into a first generation virus under the regulation of a tumour-specific promoter. In theory, following injection of the virus into a tumour, it could replicate specifically in the tumour but not in the surrounding normal cells. This type of vector could be used either to kill tumour cells directly by lysis or to deliver a "suicide gene" such as the herpes-simplex-virus thymidine-kinase gene (HSV tk) which can kill infected and bystander cells following treatment with ganciclovir.

Thus, given that the HRE construct of the present invention may be preferentially active in certain tumour tissue by virtue of the hypoxic conditions that exist within many solid tumour masses, the present invention provides an adenovirus vector comprising a polynucleotide of the invention operably linked to a nucleic acid sequence encoding an adenoviral E1a polypeptide. The E1a polypeptide under the control of the HRE enhancer would only be expressed under hypoxic conditions and therefore the adenovirus would only be replication competent under hypoxic conditions. The adenovirus lacks an endogenous E1 gene, and preferably also lacks an endogenous E3 gene. Other regions of the adenovirus genome which may be deleted are described above. It may also be desirable to include all or part of the E3 gene under the control of a hypoxia response element such that host cell immune modulation is balances to obtain the correct viral spread within the tumour and immune response to infected cells.

An adenovirus defective only for E1b has been used specifically for antitumour treatment in phase-1 clinical trials. The polypeptides encoded by E1b are able to block p53-mediated apoptosis, preventing the cell from killing itself in response to viral infection. Thus, in normal non tumour cells, in the absence of E1b, the virus is unable to block apoptosis and is thus unable to produce infectious virus and spread. In tumour cells deficient in p53, the E1b defective virus can grow and spread to adjacent p53-defective tumour cells but not to normal cells. Again, this type of vector could also be used to deliver a therapeutic gene such as HSV tk.

Consequently, it is preferred that the E1a-expressing adenoviruses of the present invention lack a functional E1b gene.

Other essential viral genes may also be placed under the control of a hypoxia responsive regulatory element.

Vectors Derived from Herpes Simplex Viruses

1. Viral Strains

The HSV vectors of the invention may be derived from, for example, HSV1 or HSV2 strains, or derivatives thereof, preferably HSV1. Derivatives include inter-type recombinants containing DNA from HSV1 and HSV2 strains. Derivatives preferably have at least 70% sequence homology to either the HSV1 or HSV2 genomes, more preferably at least 90%, even more preferably 95%.

The use of HSV strains in therapeutic procedures will require the strains to be attenuated so that they cannot establish a lytic cycle. In particular, if HSV vectors are to be used for gene therapy in humans the polynucleotide should preferably be inserted into an essential gene. This is because if a vector virus encounters a wild-type virus transfer of a heterologous gene to the wild-type virus could occur by recombination. However as long as the polynucleotide is inserted into an essential gene this recombinational transfer would also delete the essential gene in the recipient virus and prevent 'escape' of the heterologous gene into the replication competent wild-type virus population.

Attenuated strains may be used to produce the HSV strain of the present invention, here given as examples only, including strains that have mutations in either ICP34.5 or ICP27, for example strain 1716 (MacLean et al., 1991, J Gen Virol 72: 632-639), strains R3616 and R4009 (Chou and Roizman, 1992, PNAS 89: 3266-3270) and R930 (Chou et al., 1994, J. Virol 68: 8304-8311) all of which have mutations in ICP34.5, and d27-1 (Rice and Knipe, 1990, J. Virol 64: 1704-1715) which has a deletion in ICP27. Alternatively strains deleted for ICP4, ICP0, ICP22, ICP6, ICP47, vhs or gH, with an inactivating mutation in VMW65, or with any combination of the above may also be used to produce HSV strains of the invention.

The terminology used in describing the various HSV genes is as found in Coffin and Latchman, 1996. Herpes simplex virus-based vectors. In: Latchman DS (ed). Genetic manipulation of the nervous system. Academic Press: London, pp 99-114.

2. Complementing Cell Lines

HSV viruses defective in ICP27 are propagated in a cell line expressing ICP27, for example V27 cells (Rice and Knipe, 1990, J. Virol 64: 1704-1715) or 2-2 cells (Smith et al., 1992, Virology 186: 74-86). ICP27-expressing cell lines can be produced by co-transfecting mammalian cells, for example the Vero or BHK cells, with a vector, preferably a plasmid vector, comprising a functional HSV ICP27 gene capable of being expressed in said cells, and a vector, preferably a plasmid vector, encoding a selectable marker, for example neomycin resistance. Clones possessing the selectable marker are then screened further to determine which clones also express functional ICP27, for example on the basis of their ability to support the growth of ICP27$^-$ mutant HSV strains, using methods known to those skilled in the art (for example as described in Rice and Knipe, 1990).

Cell lines which do not allow reversion of an ICP27$^-$ mutant HSV strain to a strain with functional ICP27 are produced as described above, ensuring that the vector comprising a functional ICP27 gene does not contain sequences that overlap with (i.e. are homologous to) sequences remaining in the ICP27$^-$ mutant virus.

Where HSV strains of the invention comprise inactivating modifications in other essential genes, for example ICP4, complementing cell lines will further comprise a functional HSV gene which complements the modified essential gene in the same manner as described for ICP27.

3. Methods of Mutation

HSV genes may be rendered functionally inactive by several techniques well known in the art. For example, they may be rendered functionally inactive by deletions, substitutions or insertions, preferably by deletion. Deletions may remove portions of the genes or the entire gene. Inserted sequences may include the expression cassette described above.

Mutations are made in the HSV strains by homologous recombination methods well-known to those skilled in the art. For example, HSV genomic DNA is transfected together with a vector, preferably a plasmid vector, comprising the mutated sequence flanked by homologous HSV sequences. The mutated sequence may comprise deletions, insertions or substitutions, all of which may be constructed by routine techniques. Insertions may include selectable marker genes, for example lacZ, for screening recombinant viruses by, for example, β-galactosidase activity.

Mutations may also be made in other HSV genes, for example genes such as ICP0, ICP4, ICP6, ICP22, ICP47, VMW65, gH or vhs. In the case of the VMW65 gene, the entire gene is not deleted since it encodes an essential structural protein, but a small inactivating insertion is made which abolishes the ability of VMW65 to transcriptionally activate IE genes (Ace et al., 1989, J Virol 63: 2260-2269).

4. HSV Strains Comprising a Transgene and miRNA of the Invention

A transgene and mircoRNA of the invention may be inserted into the HSV genome at any location provided that the virus can still be propagated, which may require the use of a cell line carrying another HSV essential gene (as described in 2.) if the NOI is inserted into an essential gene The sequences of the invention may be inserted into the HSV genome by homologous recombination of HSV strains with, for example, plasmid vectors carrying the expression cassette flanked by HSV sequences, as described above for introducing mutations. The polynucleotide may be introduced into a suitable plasmid vector comprising HSV sequences using cloning techniques well-known in the art.

Other Viral Vectors

Other viral vectors which may be used in the present invention include adeno-associated viruses, vesicular stomatitis viruses, vaccinia viruses and SV-40-based viral vectors.

Administration

The miRNA and transgene may be administered to a patient or used to produce a transgenic plant or non-human animal. The term "administered" includes delivery by viral or non-viral techniques. Viral delivery mechanisms include but are not limited to adenoviral vectors, adeno-associated viral (AAV) vectors, herpes viral vectors, retroviral vectors, lentiviral vectors, and baculoviral vectors etc as described above. Non-viral delivery mechanisms include lipid mediated transfection, liposomes, immunoliposomes, lipofectin, cationic facial amphiphiles (CFAs) and combinations thereof.

Diseases

The delivery of one or more therapeutic genes by a vector system according to the present invention may be used alone or in combination with other treatments or components of the treatment.

For example, the vector of the present invention may be used to deliver one or more transgene(s) useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the vector of the present invention may be used to deliver one or more transgene(s) useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the retroviral vector of the present invention may be used to deliver one or more transgenes(s) useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimoorchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

The present invention also provides a pharmaceutical composition for treating an individual by gene therapy, wherein the composition comprises a therapeutically effective amount of the vector of the present invention comprising one or more deliverable therapeutic and/or diagnostic transgenes(s) or a viral particle produced by or obtained from same. The pharmaceutical composition may be for human or animal usage. Typically, a physician will determine the actual dosage which will be most suitable for an individual subject and it will vary with the age, weight and response of the particular individual.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s), and other carrier agents that may aid or increase the viral entry into the target site (such as for example a lipid delivery system).

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavemosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The delivery of one or more therapeutic genes by a vector system according to the invention may be used alone or in combination with other treatments or components of the treatment. Diseases which may be treated include, but are not limited to: cancer, neurological diseases, inherited diseases, heart disease, stroke, arthritis, viral infections and diseases of the immune system. Suitable therapeutic genes include those coding for tumour suppressor proteins, enzymes, pro-drug activating enzymes, immunomodulatory molecules, antibodies, engineered immunoglobulin-like molecules, fusion proteins, hormones, membrane proteins, vasoactive proteins or peptides, cytokines, chemokines, antiviral proteins, antisense RNA and ribozymes.

Examples

Plasmid Construction

The sequences for all miRNAs used here were obtained from the miRNA Registry (Griffiths-Jones et al., 2006) (http://www.sanger.ac.uk/Software/Rfam/mirna/index.shtml). miRNA Target (mirT) sequences were constructed as follows:

```
For 4x.mir-142-3p.Target (mir-142-3pT) the
following oligonucleotides were annealed:
5'CTAGAGTCGACTCCATAAAGTAGGAAACACTACACGATTCCATAAAGT
AGGAAACACTACAACCGGT (S1) (SEQ ID NO: 1)

5'TGTAGTGTTTCCTACTTTATGGAATCGTGTAGTGTTTCCTACTTTATG
GAGTCGACT (AS1) (SEQ ID NO: 2),

5'TCCATAAAGTAGGAAACACTACATCACTCCATAAAGTAGGAAACACTA
CAC (S2) (SEQ ID NO: 3),

5'TCGAGTGTAGTGTTTCCTACTTTATGGAGTGATGTAGTGTTTCCTACT
TTATGGAACCGGT (AS2) (SEQ ID NO: 4).
```

Ligation of these oligonucleotides created a doubled stranded DNA fragment with XbaI and XhoI sticky ends. The underlined sequences are designed to be perfectly complementary to a specific miRNA. The annealed oligonucleotides were subcloned into the XbaI and XhoI site of pBluescriptII.KS. The resulting vectors were subsequently digested with either SacII and KpnI, NheI and AgeI, or SalI, and the mirT fragment was isolated for ligation into the appropriate sites of the recipient vectors:

pCCL.sin.cPPT.PGK.GFP.WPRE to create pCCL.sin.cPPT.PGK.GFP.WPRE.mirT pCCL.sin.cPPT.PGKas.GFPas.CTEas.polyAas to create pCCL.sin.cPPT.PGKas.GFPas.mirTas.CTEas.polyAas pCCL.sin.cPPT.PGK.ΔLNGFR.WPRE to create pCCL.sin.cPPT.PGK.ΔLNGFR.mirT.WPRE pRRL.sin.cPPT.CMV.hFIX.WPRE to create pRRL.sin.cPPT.CMV.hFIX.WPRE.mirT.

pRRL.sin.cPPT.ET.hFIX.WPRE to create pRRL.sin.cPPT.ET.hFIX.WPRE.mirT.

pCCL.sin.cPPT.polyA.CTE.eGFP.minhCMV.hPGK.deltaNGFR.Wpre to create pCCL.sin.cPPT.polyA.CTE.mirT.eGFP.minhCMV.hPGK.deltaNGFR.Wpre.

Large scale preparation of DNA was carried out using the Marlingen Biosciences endotoxin-free high purity plasmid maxi prep system.

Vector Production and Titration

VSV-pseudotyped third-generation LVs were produced by transient four-plasmid cotransfection into 293T cells and purified by ultracentrifugation as described (De Palma and Naldini, 2002). Expression titer of GFP was estimated on 293T cells by limiting dilution. Vector particles were measured by HIV-1 gag p24 antigen immunocapture (NEN Life Science Products). Concentrated vector expression titer ranged from $0.15-1.5 \times 10^{10}$ transducing units$^{293T}$ (TU)/ml for all vectors.

Cell Cultures 293T cells were maintained in Iscove's modified Dulbecco's medium (IMDM; Sigma) supplemented with 10% fetal bovine serum (FBS; Gibco) and a combination of penicillin-streptomycin and glutamine. The U937 monocyte cell line was maintained in RPMI supplemented as above (complete RPMI). Primary cultures of human dendritic cells were isolated from peripheral blood as previously described and maintained in complete RPMI supplemented with GM-CSF and IL-4 (Bender et al., 1996).

DNA and RNA Extraction

DNA from cells and tissues was extracted by using "Blood & Cell Culture DNA Midi Kit" (Qiagen, Hilden, Germany), according to manufacturer's instructions. RNA from cells was extracted by using "Tri Reagent" (Sigma, Saint Louis, Mo.), according to manufacturer's instructions.

Northern Blot

Northern Blot was performed as previously described (De Palma and Naldini, 2002). Twenty micrograms of total RNA were loaded and 100 ng $^{32}$P labelled-GFP probe was used.

Vector Copy Number Quantification

Vector C/G were quantified by real-time PCR, starting from 100 ng template DNA extracted from mouse tissues or 200 ng template DNA extracted from cell lines. The sets of primers and probe used for the analysis are the following:

```
LV backbone:
750 nmol forward primer (F):
5'TGAAAGCGAAAGGGAAACCA3'
(SEQ ID NO: 5), 200 nmol reverse primer (R):
5'-CCGTGCGCGCTTCAG-3'
(SEQ ID NO: 6), 200 nmol probe (P):
5'-VIC-CTCTCTCGACGCAGGACT-MGB-3'
(SEQ ID NO: 7);

murine genomic DNA: β-actin:
300 nmol F:
5'-AGAGGGAAATCGTGCGTGAC-3'
(SEQ ID NO: 8), 750 nmol R:
5'-CAATAGTGATGACCTGGCCGT-3'
(SEQ ID NO: 9), 200 nmol P:
5'-VIC-CACTGCCGCATCCTCTTCCTCCC-MGB-3'
(SEQ ID NO: 10),
```

```
-continued
human genomic DNA: hTERT:
200 nmol F:
5'-GGCACACGTGGCTTTTCG-3'
(SEQ ID NO: 11), 600 nmol R:
5'-GGTGAACCTCGTAAGTTTATGCAA-3'
(SEQ ID NO: 12), 200 nmol P:
5'-6FAM-TCAGGACGTCGAGTGGACACGGTG-TAMRA-3'
(SEQ ID NO: 13).
```

For standard curves serial dilutions of DNA from a transgenic mouse or human cell line with known number of LV integrations (determined by Southern Blot) were used. Reactions were carried out in triplicate in an ABI Prism 7900 HT Sequence Detection System (Applied Biosystems). C/G was calculated by: (ng LV/ng endogenous DNA)×(no of LV integrations in the standard curve).

Gene Expression Analysis

Reverse Transcription was carried out on 2 μg total RNA using the Random Hexamers protocol of the Superscript III First-Strand Synthesis System for RT-PCR (Invitrogen, Carlsbad, Calif.). Quantitative PCR analysis was performed to quantitate the concentration of GFP mRNA, and GAPDH expression was used for normalization. Two sets of primers and probe were used:

```
For GFP, 20X Assay on Demand (Applied Biosystems),
F: 5'-CAGCTCGCCGACCACTA-3'
(SEQ ID NO: 14), R: 5'-GGGCCGTCGCCGAT-3'
(SEQ ID NO: 15)
and

P: 5'-6FAM-CCAGCAGAACACCCCC-MGB-3'
(SEQ ID NO: 16), and for GAPDH:
200 nmol F:
5-ACCACAGTCCATGCCATCACT-3',
(SEQ ID NO: 17), 900 nmol R:
5'-GGCCATCACGCCACAGSTT-3'
(SEQ ID NO: 18)
and 200 nmol P:
5'-TET-CCACCCAGAAGACTGTGGATGCC-TAMRA-3'.
(SEQ ID NO: 19).
```

Reactions were carried in triplicate in an ABI Prism 7900 HT Sequence Detection System (Applied Biosystems).

miRNA Expression Analysis miRNA detection was carried out using the Applied Biosystems Taqman microRNA Assay system according to the manufacturer's instructions. Results were normalized to has-mir-16 and let-7a was used as a calibrator. Values are reported relative to the expression of let-7a.

Flow Cytometry

Transduced 293T cells were grown for at least 14 days before FACS analysis to reach steady state GFP expression and to rule out pseudotransduction. Before FACS analysis, adherent cells were detached with 0.05% trypsin-EDTA, washed and resuspended in PBS containing 2% FBS. Cells grown in suspension were washed and resuspended in PBS containing 2% FBS. For immunostaining, $10^5$ cells were blocked in PBS, 5% human serum, 2% FBS for 15 min at 4° C. After blocking, R-phycoerythrin (RPE)-conjugated antibodies (anti-ΔLNGFR or anti-CD45, BD Pharmingen, San Diego, Calif.) were added and the cells were incubated for 30 min at 4° C., washed, and analyzed by two-color flow cytometry on a Beckman Coulter Cytomics FC500 (Beckman Couler, Miami, Fla.).

In Vivo Vector Administration 6-8 week old Nude and Balb/c mice were purchased from Charles Rivers Laboratories (Milan, Italy) and maintained in specific-pathogen-free conditions. Hemophilia B (Clotting Factor IX knock-out) mice were a acquired from the Salk Institute (La Jolla, Calif.), and bred and maintained in specific-pathogen-free conditions. Vector administration was carried out by tail vein injection on mice. All animal procedures were performed according to protocols approved by the Hospital San Raffaele Institutional Animal Care and Use Committee.

Transgenesis

Transgenic mice were generated using LVs as described (Lois et al., 2002). Briefly, female FVB mice were superovulated with a combination of pregnant mare serum and human chorionic gonadotropin. On average between 20 and 30 embryos were collected per female and microinjected into the perivitelline space with 10-100 pl of 5×10$^7$ TU/ml LV stock on the same day. Manipulated embryos were immediately implanted into the oviduct of pseudopregnant CD1 mice. Pups were genotyped for the presence of the GFP sequence by PCR. Positive mice were bred to test germline transmission of the transgene. DNA was extracted from the tail and used to quantify vector copy number by real-time PCR in founder and F1 progeny mice.

Immunohistochemistry

For immunofluorescence, tissues were fixed in 4% paraformaldehyde, equilibrated in 20% sucrose in PBS for 48 hours at 4° C., embedded in optimal cutting temperature (OCT), and frozen. Cryostate sections (5-μm thick) were postfixed with paraformaldehyde, blocked in 5% goat serum (Vector Laboratories, Burlingame, Calif.), 1% bovine serum albumin (BSA), 0.1% Triton in PBS, and incubated with either rat anti-mouse F4/80 (Serotec, Raleigh, N.C.) or anti-mouse CD45, CD31 or CD8 (BD Pharmingen). Fluorescent signals from single optical sections were acquired by 3-laser confocal microscope (Radiance 2100; Bio-Rad, Hercules, Calif.).

Factor IX (hFIX) Quantification hF.IX concentration was determined in mouse citrated plasma by an enzyme-immunoassay for the factor IX:Ag (Roche, Milan, Italy), and for FIX activity by an activated partial thromboplastin time (aPTT) assay, as previously described (Brown et al., 2004b).

Results

Figure 2:
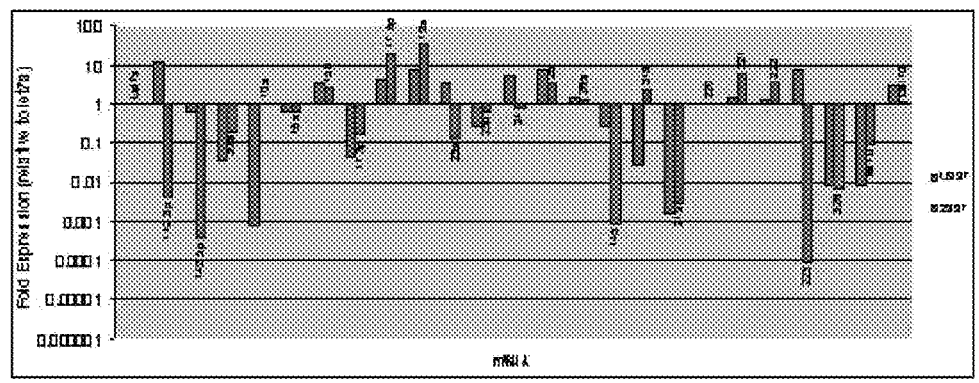
FIG. 2*a*. miRNA profiling analysis. Expression analysis of selected miRNAs in 293T and U937 cells by real-time PCR. Expression levels are reported relative to let-7a, a constitutively expressed, 'housekeeping' miRNA.
FIG. 2*b*. miRNA regulation can be used to de-target expression from hematopoietic lineages. FACS analysis of 293T (kidney origin), U937 (monocyte origin) and primary dendritic cells (peripheral blood-derived) transduced with dose-matched concentrations of the indicated LV at 14 days post-transduction. An LV containing the liver-specific Albumin promoter (LV.ALB3.GFP), is shown for comparison of off-target activity of this promoter. The histograms are representative of three independent experiments. Vector copies per genome (C/G) were determined by Taqman analysis. Shown in grey are the untransduced cells.
FIG. 2*c*. miRNA regulation can be exploited to construct a vector for divergent regulation of two transgenes. FACS analysis of GFP and ΔLNGFR expression from 293T and U937 cells transduced with closely matched concentrations of Bd.LV expressing GFP, with or without the mir-142-3pT, and ΔLNGFR, 14 days post-transduction. Dotplots are representative of two independent experiments.
FIG. 2*d*. The miRNA-regulated vector design can be used to construct a variety of vectors which are regulated by different endogenous miRNA, and mediate diverse vector expression profiles. FACS analysis of GFP and ΔLNGFR expression from 293T and U937 cells transduced with closely matched concentrations of Bd.LV expressing GFP, with or without the indicated mirT sequences, and ΔLNGFR, at 14 days post-transduction.
Figure 2:
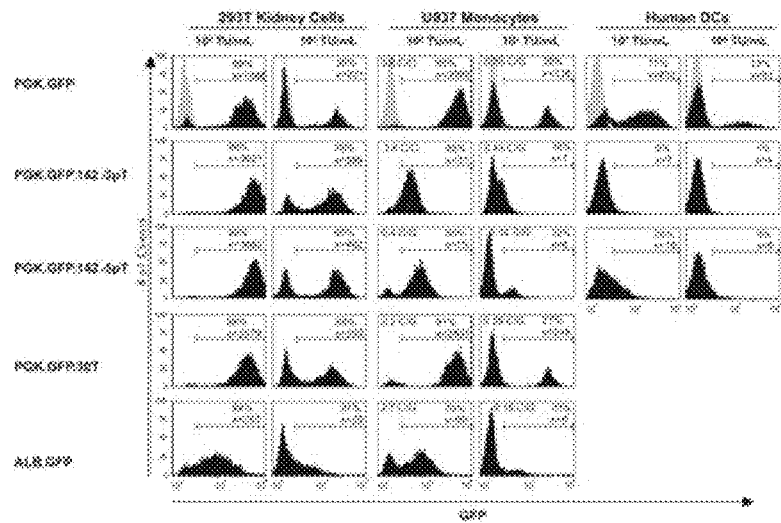
Figure 2:
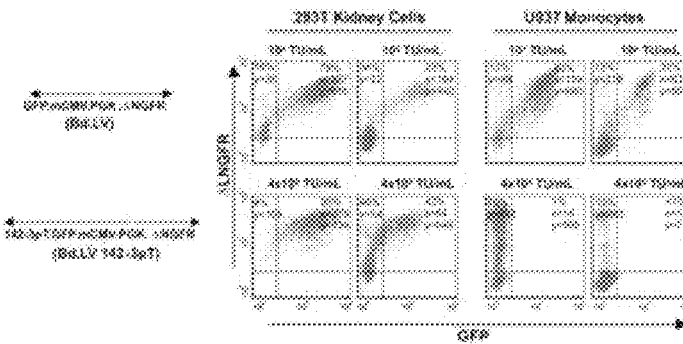
Figure 2:
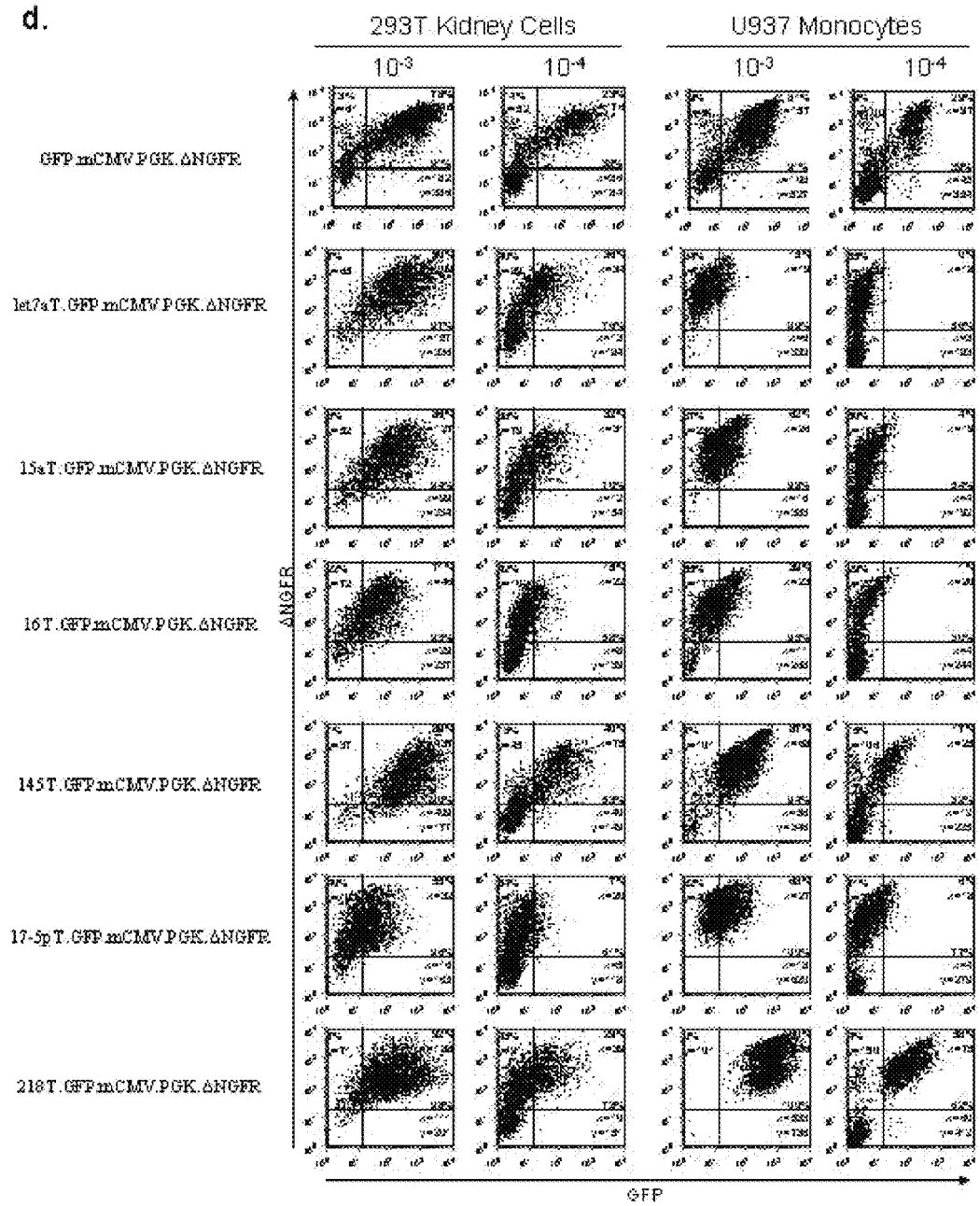

In order to create an integrating vector system with de-targeted expression profile we took advantage of the recently identified miRNA-mediated post-transcriptional silencing system. We constructed a miRNA-regulated lentiviral vector (LV) by inserting four tandem copies of a 23 bp sequence (mirT) with perfect complementarity to either mir-30a, mir-142-5p or mir-142-3p into the 3'-untranslated region (3'UTR) of a GFP expression cassette driven by the ubiquitously expressed Phosphoglycerate Kinase (PGK) promoter (FIG. 1a). This design, using multiple copies of a perfectly complementary target, is intended to optimize repression of the transgene in the presence of the miRNA, and is based on an emerging understanding of the rules governing miRNA-mediated regulation (Bartel and Chen, 2004; Doench et al., 2003). mir-142-5p and mir-142-3p were chosen because recent reports, using Northern blot and microarray analysis, indicate that these miRNAs are enriched in hematopoietic cells (Baskerville and Bartel, 2005; Chen et al., 2004). We confirmed these previous findings by carrying out quantitative real-time PCR analysis to determine the concentration of specific miRNAs in our target cells (FIG. 2a). As shown in FIG. 2a, mir-142-3p and mir-142-5p are highly expressed in U937 cells, but detected only at low levels in 293T cells. mir-30a was found to be low in both 293T and U937 cells, and thus serves as a control for our studies.

Vectors were prepared and concentrated as previously described. Titration of the miRNA-regulated LV indicated that inclusion of the target sequence did not adversely affect vector infectivity or the levels of transgene expression in non-hematopoeitic cells (FIG. 2b). Levels of transduction and transgene expression were achieved that were comparable to the parent vector without the miRNA target sequence (LV.PGK.GFP). In contrast, transduction of both the human U937 monocyte cell line or human primary dendritic cells resulted in drastically different expression profiles between the two vectors, LV.PGK.GFP and LV.PGK.GFP.142-3pT. In U937 cells, mean fluorescence intensity was 50-100-fold higher in cells transduced with LV.PGK.GFP even though Taqman analysis revealed similar copies of vector per genome (C/G). A similar finding was also observed in dendritic cells, where even after transduction at high vector concentration (>50 MOI), there was a near complete abrogation of transgene expression in cells receiving the LV.PGK.GFP.142-3pT vector. As a control vector, the target sequence of mir-30a was cloned into LV.PGK.GFP to create LV.PGK.GFP.mir-30aT. mir-30a is not expressed in hematopoietic cells (Zeng et al., 2002), and, as expected, we did not see any reduction in GFP expression following cell transduction. Thus, our results clearly demonstrate that in human cells our vector design maintains high vector infectivity, while preventing gene expression in particular cell types.

We previously described a vector system that took advantage of the bidirectional activity of a single promoter element to coordinately express two distinct transcripts (Amendola et al., 2005). This system enables two transgenes to be expressed in a cell following transduction with a single vector. While this system is useful for many gene therapy applications, there are also circumstances in which it may be necessary to express only one of the two transgenes. Unfortunately, there is no gene transfer system currently available which permits divergent regulation of two transgenes from a single vector.

In order to develop a divergently regulated vector system, we modified a bidirectional LV (Bd.LV) to include the mir-142-3pT in the 3'UTR of the GFP reporter cassette (FIG. 1b). This vector exploits the intrinsic bidirectional activity of the PGK promoter to drive divergent transcription of two transgenes. Transduction of 293T cells revealed no differences in GFP or low-affinity nerve growth factor receptor (ΔLNGFR) expression between Bd.LV with or without the mirT (FIG. 2c). However, in transduced monocytes, the Bd.LV without the mirT expressed both GFP and ΔLNGFR, whereas the tagged vector only expressed ΔLNGFR. This indicates that repression of the tagged transgene is occurring at the post-transcriptional level, and not by transcriptional silencing, since silencing of the promoter would have prevented the expression of both transgenes. These results also demonstrate the utility of our miRNA-regulation strategy, in combination with the bidirectional vector system, for providing a vector design, which can be used divergently regulated two transgenes from a single vector.

To further demonstrate the versatility of this approach, we selected a panel of miRNAs based on their differential expression in 293T and U937 cells (FIG. 2a), and cloned the target sequences of these miRNAs into the GFP expression cassette of the Bd.LV vector. As shown in FIG. 2d, transduction of the two cell populations revealed highly diverse expression patterns between each of the vectors. Importantly, concentration of the miRNA, as determined by real-time PCR, showed strong correlation with the degree of suppression observed. For example, GFP expression from 218T.GFP.mCMV.PCK.ΔNGFR was reduced more then 10-fold in 293T cells, but little or no suppression was observed in U937 cells, where mir-218 is expressed to only low levels. Thus, this data extends the potential utility of our approach to other miRNAs, and demonstrates that expression profiling can provide a simple means to design a vector system with a desired tissue expression pattern.

Figure 3:
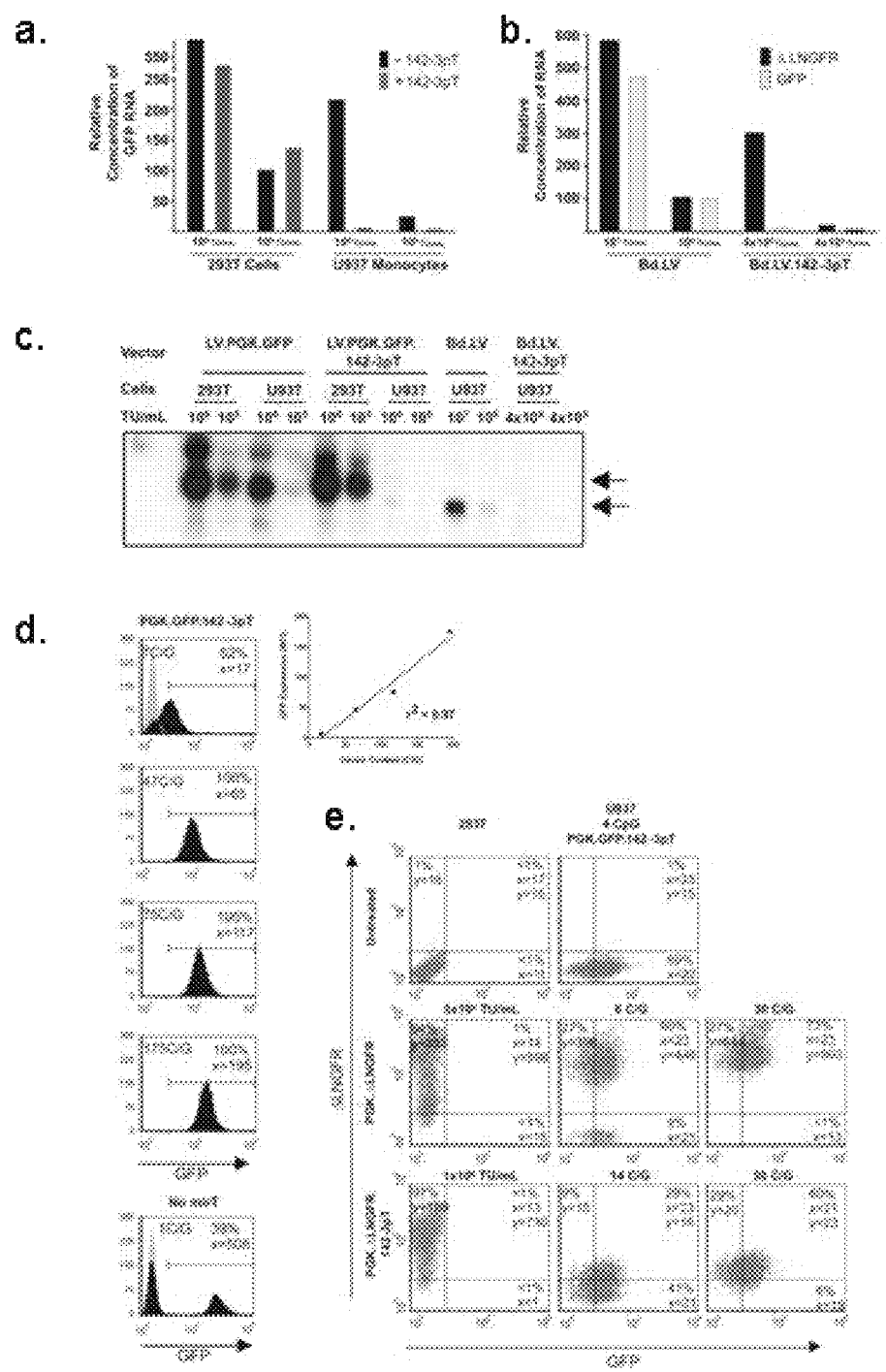
FIG. 3a. Quantitative RT-PCR analysis of GFP expression from 293T and U937 cells transduced by LV.PGK.GFP or LV.PGK.GFP.142-3pT. cDNA is from cells presented in FIG. 1b. All samples were normalized to GAPDH expression and values are reported relative to transcripts detected from 293T cells transduced with $10^5$ TU/mL LV.PGK.GFP, which was set as the calibrator.
FIG. 3b. Quantitative RT-PCR analysis of GFP and ΔLNGFR expression from U937 cells transduced by the indicated Bd.LV. The cDNA was taken from the cells presented in FIG. 1c. All values are reported relative to the level of ΔLNGFR transcripts detected in cells transduced with $10^5$ TU/mL Bd.LV.
FIG. 3c. Northern blot analysis of cells transduced by LV and BDd.LV with or without mir-142-3pT (shown in FIGS. 1b and 1c, respectively). Twenty micrograms of total RNA was loaded for each sample and probed for GFP. The expected size of the GFP transcript is indicated by arrows for the LV (top) and Bd.LV (bottom).
FIG. 3d. U937 cells repeatedly infected with LV.PGK-.GFP.142-3pT to obtain increasing vector content. GFP was measured by FACS analysis. Average vector C/G for the cell population are indicated. A regression analysis showing the relationship between increasing vector dose and transgene expression for LV.PGK.GFP.142-3pT is included (right). Note that in U937 cells a single copy of LV.PGK.GFP (bottom left panel) expresses GFP to higher levels than 175 C/G of LV.PGK.GFP.142-3pT.
FIG. 3e. The robustness of mir-142-3p-mediated RNA interference was measured by superinfection of U937 cells containing 4 C/G of LV.PGK.GFP.mir-142-3pT with increasing concentrations of LV.PGK.ΔLNGFR.mir-142-3pT. Taqman analysis was used to detect the vector copy number of superinfected cells, and changes in GFP and ΔLNGFR expression were measured by FACS analysis.

Because little is known about the robustness of miRNA activity we set out to determine whether there was a threshold of regulation that would be overcome by increasing the vector copies carrying mirTs in target cells. Following multiple rounds of transduction of U937 cells there was only an incremental rise in transgene expression, which was linearly related to the vector C/G (FIG. 3d). These results indicate that suppression was maintained to the same extent for all vector doses tested, and that saturation is not reached even at 175 vector C/G. We next asked whether expressing exogenous sequences carrying mirTs could squelch the endogenous miRNA from its natural targets. Because no target mRNAs have been identified for mir-142-3p, we overloaded cells with a second vector carrying the same mirT in a different expression cassette. U937 cells carrying 4 C/G of LV.PGK.GFP.142-3pT were superinfected with LV.PGK.ΔLNGFR.142-3pT, and, as shown in FIG. 3e, even after the introduction of 30 copies of a new vector, there was no increase in GFP expression. In addition, ΔLNGFR expression was suppressed by mir-142-3p (FIG. 3e). Overall, our data suggest that mir-142-3p is not reaction-limiting in the RNA interference pathway, and that the introduction of new genetic material, containing the mir-142-3pT, should not perturb the natural activity of this miRNA.

The novelty of the miRNA regulation strategy provides the possibility to engineer vectors in manners not previously possible. In addition to its usefulness for preventing expression in hematopoietic cells, we sought to use miRNA regulation to selectively prevent transgene expression in vector producer cells. Normally during the process of vector production, in addition to expression of the vector genome from the transfer plasmid, there is also expression of the transgene. In the case of vectors encoding toxic molecules this can be particularly problematic, since expression of the toxic protein kills the producer cells and leads to an overall reduction in vector titer. Thus, the ability to selectively prevent transgene expression in producer cells would be a major advancement for production of specific vectors, such as those encoding toxic molecules.

Our miRNA profiling data revealed that mir-19a is highly expressed in 293T cells. This miRNA has previously been shown to be associated with cancer, but not found in normal tissue, and may account for its high expression in transformed and tumor cell lines. We reasoned that inclusion of the mir-19aT sequence would prevent transgene expression in 293T producer cells. In order not to decrease vector titer, we constructed the vector so that the expression cassette, including the 19aT sequence, would be in antisense. In this configuration, the vector genome can be transcribed, and because the 19aT sequence is in antisense orientation the transcript will not be subject to degradation by mir-19a-mediated RNAi.

Figure 4:
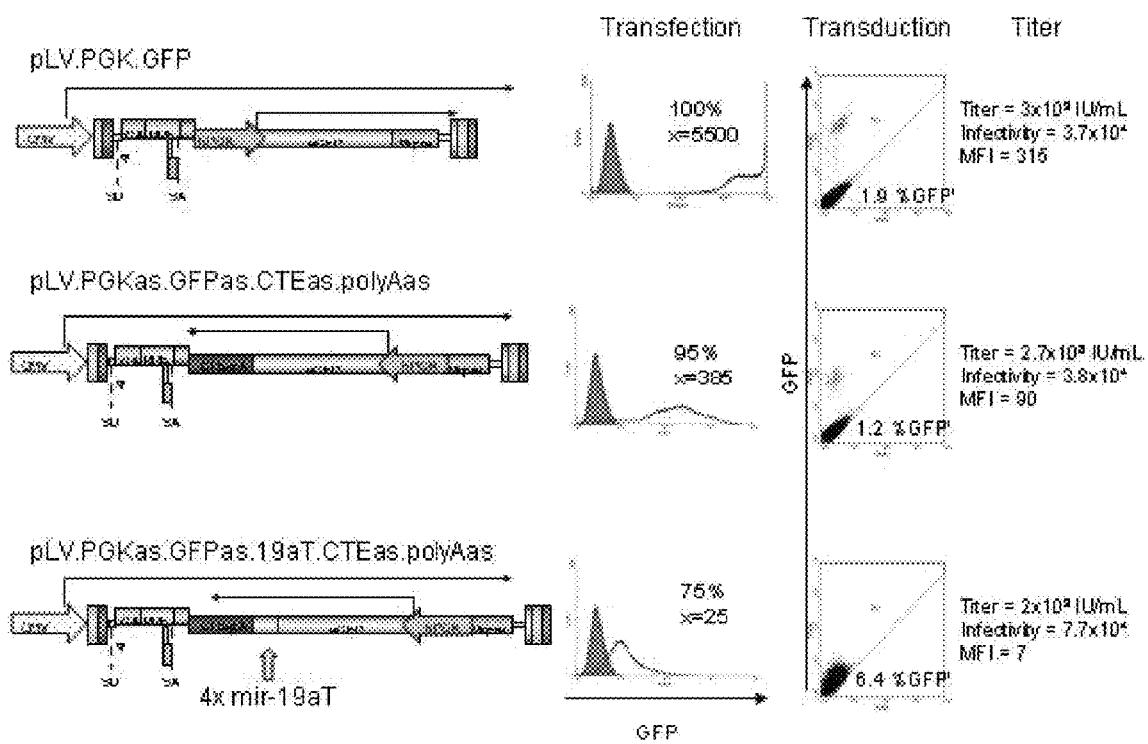
FIG. 4. miRNA regulation can be exploited to prevent transgene expression in producer cells without reducing vector titer. Transgene expression and production titer of three different lentiviral vector constructs were compared. Histograms show the GFP expression in 293T cells during vector production. Dotplots present the GFP expression in 293T cells following transduction with the produced vectors. Constructs pLV.PGKas.GFPas.CTEas.polyAas and pLV.PGKas.GFPas.19aT.CTEas.polyAas have the expression cassettes in antisense orientation. As shown, when the expression cassette is placed in antisense (pLV.PGKas.GFPas.CTEas.polyAas) there is a 10-fold reduction in vector titer when compared to the canonical pLV.PGK.GFP vector. However, inclusion of the mir-19aT sequence in the antisense expression cassette restores the titer to that of the canonical construct.

As shown in FIG. 4, upon transient transfection of 293T, there was a more then 100- and 10-fold reduction in GFP expression between pLV.PGKas.GFPas.19aT.CTEas.polyAas and pLV.PGK.GFP and pLV.PGKas.GFPas.CTE-as.polyAas, respectively. Thus indicating that inclusion of the mir-19aT sequence can prevent gene expression in 293T cells. Importantly, unlike pLV.PGKas.GFPas.CTE-as.polyAas, which resulted in a 10-fold reduction in vector titer compared to the canonical plasmid, which is due to the antisense affect of complementry transcripts produced by the plasmid, pLV.PGKas.GFPas.19aT.CTEas.polyAas did not produce a vector with lower titer then the pLV.PGK.GFP construct. Thus, our data demonstrates that miRNA regulation can be used to prevent expression of a transgene during vector production without negatively affecting vector titer.

Figure 5:
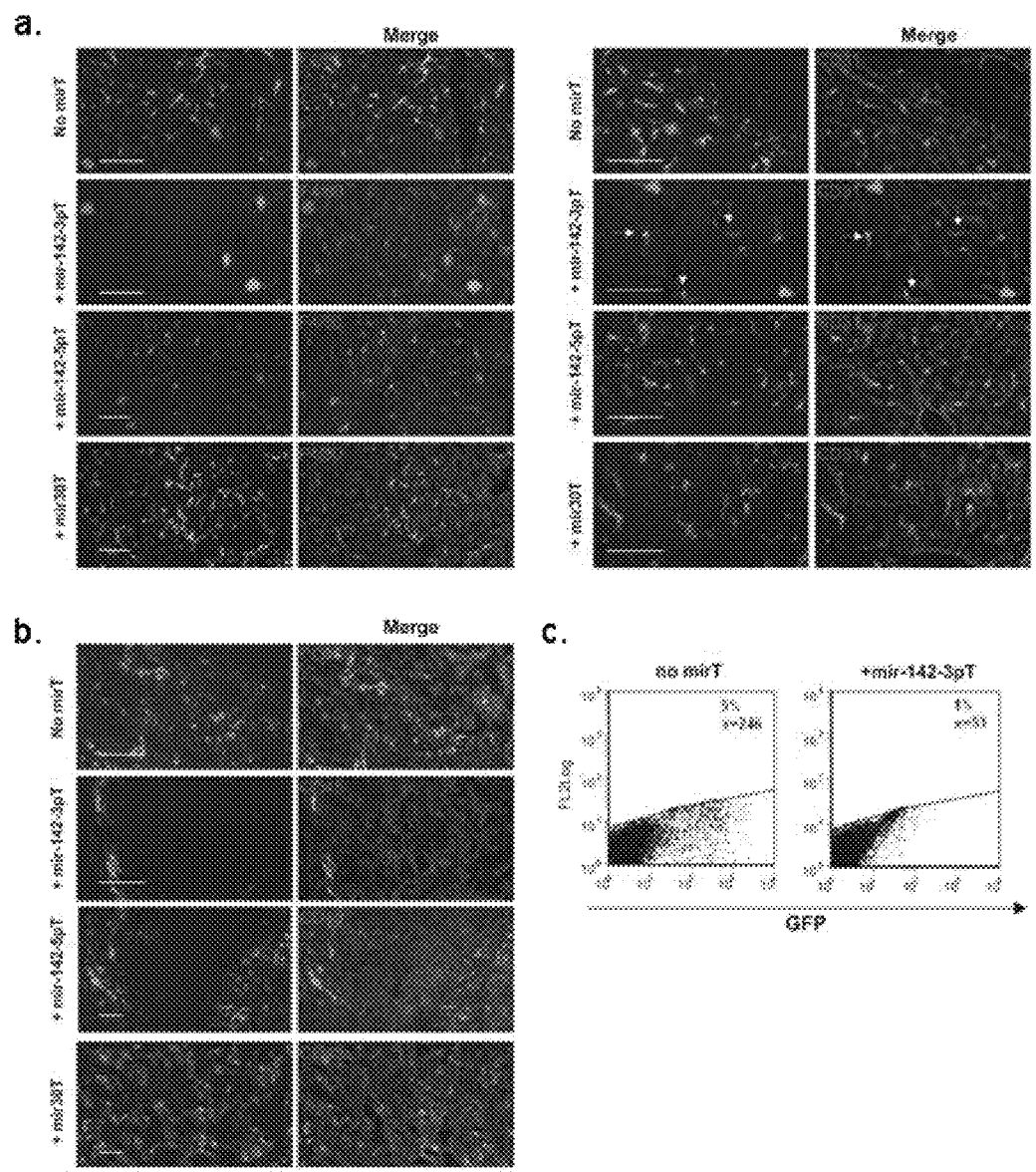
FIG. 5a. miRNA-regulated vectors can be designed to achieve selective de-targeting of expression from a particular cellular lineage in vivo. Confocal microscopy analysis of liver of nude mice injected by tail vein 2 weeks prior with the indicated LV. Images are representative of 3 mice. GFP was visualized by direct fluorescence. Liver sections were immunostained for (left) the macrophage-specific marker F4/80 and (right) for the endothelial cell marker CD31. Virtually none of the F4/80+ Kupffer cells expressed GFP to detectable levels when the mir-142-3pT vector was used, whereas many of these cells expressed GFP when transduced by the other vectors. Note that the CD31+ liver sinusoidal endothelial cells expressed GFP upon transduction by all vectors, including LV.PGK.GFP.142-3pT (arrows).
FIG. 5b. miRNA-regulated vectors can be designed to achieve selective de-targeting of expression from a particular cellular lineage in vivo. Spleen sections from the same mice as above were immunostained for the pan-leukocyte CD45 marker. LV.PGK.GFP.142-5pT effectively de-targeted GFP expression from the CD45+ leukocytes, but permitted strong GFP expression in the non-hematopoietic stromal cells (CD45-negative) of the marginal zone sinus.
FIG. 5c. miRNA-regulated lentiviral vectors can be designed to prevent transgene expression in hematopoietic cells following intravenous vector injection. FACS analysis of GFP expression from splenocytes of LV.PGK.GFP- and LV.PGK.GFP.142-3pT-treated animals.

Following in vitro characterization of our miRNA-regulated LV in human cells, we extended our studies to the mouse. Mice express exact homologs of each of the human miRNAs we tested in vitro, although their tissue expression patterns have not been established in situ (Lagos-Quintana et al., 2002). Nude mice were administered $2\times10^8$ LV particles. Quantitative PCR (Q-PCR) analysis of the spleen and liver revealed similar vector content for all treatment groups (data not shown). Expression profiles, however, differed dramatically. LV.PGK.GFP and LV.PGK.GFP.30aT treated animals showed a widespread pattern of cell expression within the liver, including Kupffer cells, hepatocytes and endothelial cells (FIG. 5a). In contrast, LV.PGK.GFP.142-3pT-treated animals had almost undetectable GFP expression in Kupffer cells, but maintained high levels of GFP in hepatocytes and endothelial cells.

Consistent findings were observed in the spleen of treated animals. In mice receiving the LV.PGK.GFP vector there was a high frequency of GFP+ splenocytes (>5%), with strong levels of expression, as indicated by FACS analysis (FIG. 5c). In comparison, less than 1% of splenocytes from LV.PGK.GFP.142-3pT-treated animals were GFP+ and only at low intensity. Immunohistochemical analysis of these mice revealed the presence of GFP+ cells found almost exclusively in the marginal zone. These cells were not of hematopoietic lineage, as indicated by the negative co-staining for the pan-leukocyte marker CD45 (FIG. 5b), but were likely reticular fibroblasts (Steiniger et al., 2003), part of the supporting stroma of the spleen. This demonstrates a novel aspect of this approach, in which gene expression can be maintained in a wide variety of cell types, while restricting expression from a particular cellular lineage.

Figure 6:
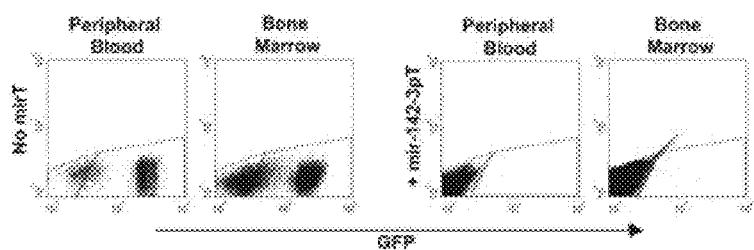
FIG. 6a. miRNA-regulated vectors can be designed to prevent transgene expression in hematopoietic lineage cells in vivo, even at high vector copy. FACS analysis of GFP expression in the peripheral blood and bone marrow from representative TgN.PGK.GFP.142-3pT (24 C/G) and TgN-.PGK.GFP (4 C/G) transgenic mice showing virtually undetectable transgene expression despite the high number of vector copies carried by these mice.
FIG. 6b. miRNA-regulated vectors can be designed to segregate gene expression between hematopoietic and non-hematopoietic lineages of transgenic mice. Immunofluorescence of the indicated organs from the above mice. GFP was visualized by direct fluorescence. Hematopoietic lineage cells were marked by CD45 immunostaining in all organs analyzed except for the thymus, where CD3 was used to mark thymocytes. In TgN.PGK.GFP mice, pan-cellular GFP expression was detected in the parenchyma and stroma of all organs. Hematopoietic lineage cells appear yellow because of overlap between CD45 staining and GFP expression. In contrast, GFP expression in PGK.GFP.142-3pT transgenic mice was selectively suppressed in the CD45+ Kupffer cells (liver), alveolar (lung) and lamina propria (gut) macrophages, which appear red and are indicated by arrows. In the spleen and thymus, GFP expression was also negative in all hematopoietic lineage cells, despite strong expression within the stroma of these organs.
Figure 6:
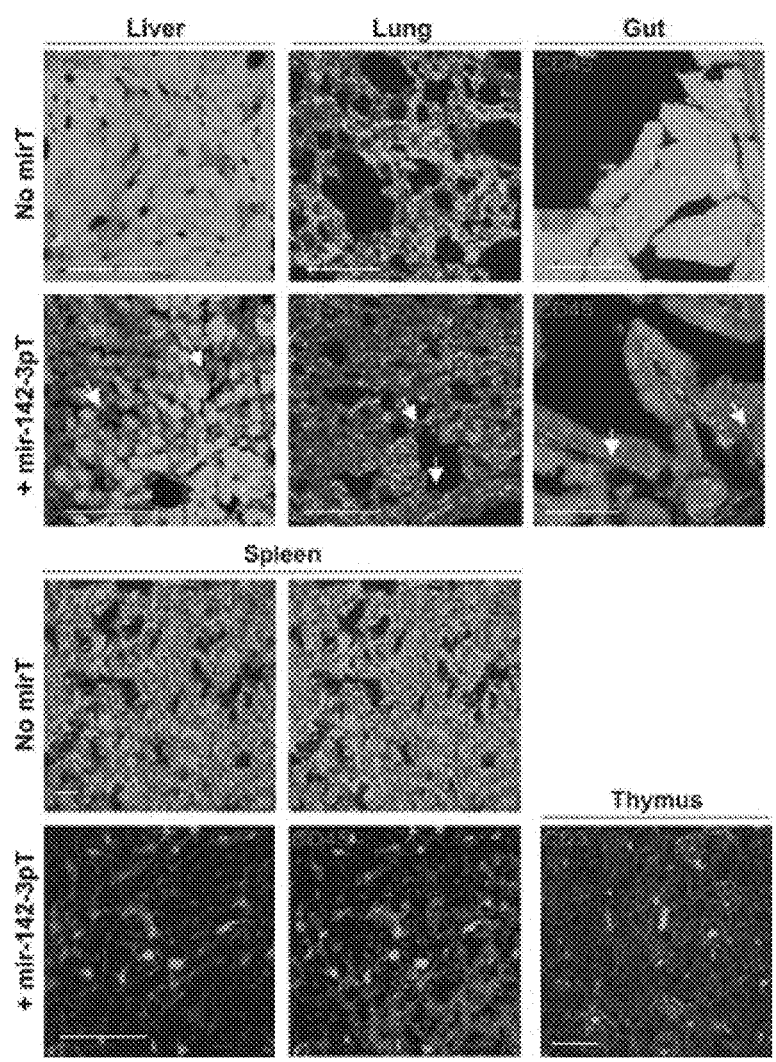

To better characterize the expression profile of our vector, and correspondingly, the regulatory activity of mir-142-3p, transgenic mice were generated using the LV.PGK.GFP.142-3pT vector. The peripheral blood of F1 progeny carrying a range of vector C/G (from 4 to 24) were analyzed, and GFP expression was virtually undetectable in all hematopoietic lineages (n=26; FIG. 6a). Moreover, despite bright, pan-cellular fluorescence throughout the parenchyma of liver, gut and lung, as well as the stromal architecture of the spleen, thymus, and bone marrow, we observed no GFP expression within the hematopoietic lineage cells of these organs (FIG. 6b). These results demonstrate that endogenous mir-142-3p sharply and robustly restricts transgene expression from hematopoietic lineages.

Figure 7:
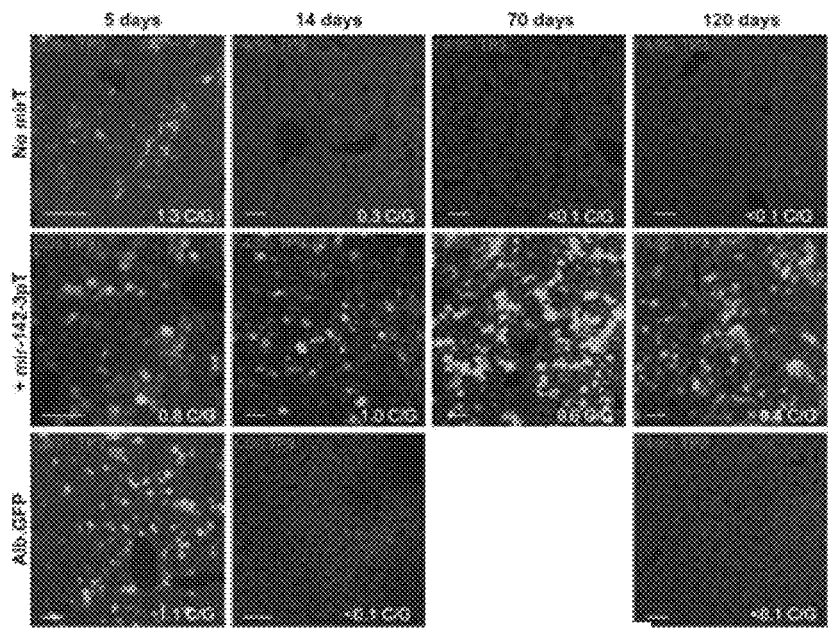
FIG. 7a. miRNA-regulated LV enables stable gene transfer in immunocompetent mice. Confocal immunofluorescence analysis of liver and spleen sections from Balb/c mice administered the indicated LV. GFP was visualized in the liver by direct fluorescence; Kupffer cells, CD8+ T-cells, or endothelial cells were detected by staining with anti-F4/80, anti-CD8, or anti-CD31, respectively. The GFP+ cells of LV.PGK.GFP and LV.ALB.GFP mice were cleared from the liver by 2 weeks, which correlated with the presence of CD8+ T-cell infiltrates. In contrast, abundant GFP+ hepatocytes and endothelial cells persisted for >120 days (longest time point analyzed) in mice injected with LV.PGK-.GFP.142-3pT.
FIG. 7b. GFP+ cells in the liver of day 70 LV.PGK-.GFP.142-3pT-treated mice had the typical morphology of hepatocytes or were CD31+ endothelial cells (arrows). This demonstrates a novel aspect of this approach, which is selective de-targeting of expression from a particular cell type, while permitting transgene expression in a broad range of cell lineages.
FIG. 7c. Hematoxylin and eosin (H&E) staining showing normal histology and absence of mononuclear cell infiltration in LV.PGK.GFP.142-3pT mice at 42 days post-injection FIG. 7d. Analysis of the spleen of immunocompetent mice injected 5 days prior with the indicated vector. GFP expression from the mir-142-3pT vector was mainly observed at the marginal zone sinus (MS); some of these GFP+ cells expressed α-smooth muscle actin (α-SMA) and were identified as fibroblast-like stromal cells (arrows). Note that scattered GFP+ cells, including some CD45+ hematopoietic cells, were present in the spleen of LV.ALB. GFP mice (arrow). This further demonstrates that the miRNA-regulation strategy can provide an improved means of transgene regulation over tissue-specific promoters.
Figure 7:
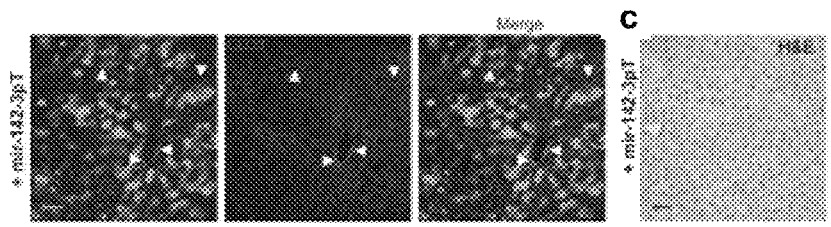
Figure 7:
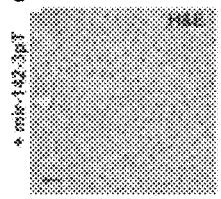
Figure 7:
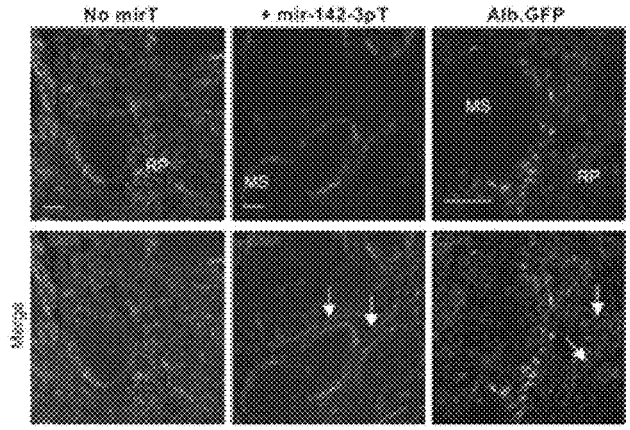

Finally, we evaluated the utility of our miRNA-regulated LV for systemic gene transfer in immunocompetent adult Balb/c mice. We administered $5\times10^8$ Transducing Units (TU)/mouse of either LV.PGK.GFP, LV.PGK.GFP.142-3pT or an LV expressing GFP under the control of the albumin promoter (LV.ALB.GFP). Mice were analyzed at various times for expression of GFP, a strong neo-antigen (Stripecke et al., 1999), in the spleen and liver. In LV.PGK.GFP-treated mice, GFP+ cells were detected at day 5, but, consistent with our previous findings (Follenzi et al., 2004), by day 14 little or no GFP+ cells were observed and vector content had declined to almost undetectable levels (FIG. 7a). Clearance of GFP+ cells also occurred with LV.ALB3.GFP, despite expression being predominately confined to hepatocytes. Notably, however, off-target expression from this vector was detected in the spleen, including within a small fraction of hematopoietic cells, and may have had a role in the initiation of immune-mediated vector clearance (FIG. 7d).

In contrast to our findings with LV.PGK.GFP and LV.ALB.GFP, GFP+ hepatocytes and endothelial cells were present to high frequency in the liver of all LV.PGK.GFP.142-3pT-treated mice at all time points analyzed (>120 days, FIG. 7a,b). Morphometric analysis indicated that between 10 to 20% of hepatocytes were GFP+ (n=10), and, importantly, the frequency of positive cells remained stable. Vector C/Gs were initially similar for all treatment groups, but by day 14 they rapidly diminished in LV.PGK.GFP and LV.ALB.GFP mice, and were maintained to well-detectable levels in LV.PGK.GFP.142-3pT-treated animals. A slow decline in C/G was observed at the longest follow-up, but because this decline did not coincide with a decrease in GFP+ hepatocytes, it was likely due to the replacement of transduced Kupffer cells during normal hematopoietic cell turnover Despite extensive GFP expression in the liver, we did not detect any GFP+ Kupffer cells. Moreover, while we did observe GFP+ reticular fibroblasts in the marginal zone of the spleen, transgene expression was not detected in hematopoietic lineage cells. Consistent with the sustained GFP expression, we did not observe significant CD8+ infiltration or signs of pathology in the liver (FIG. 7c).

Figure 8A:
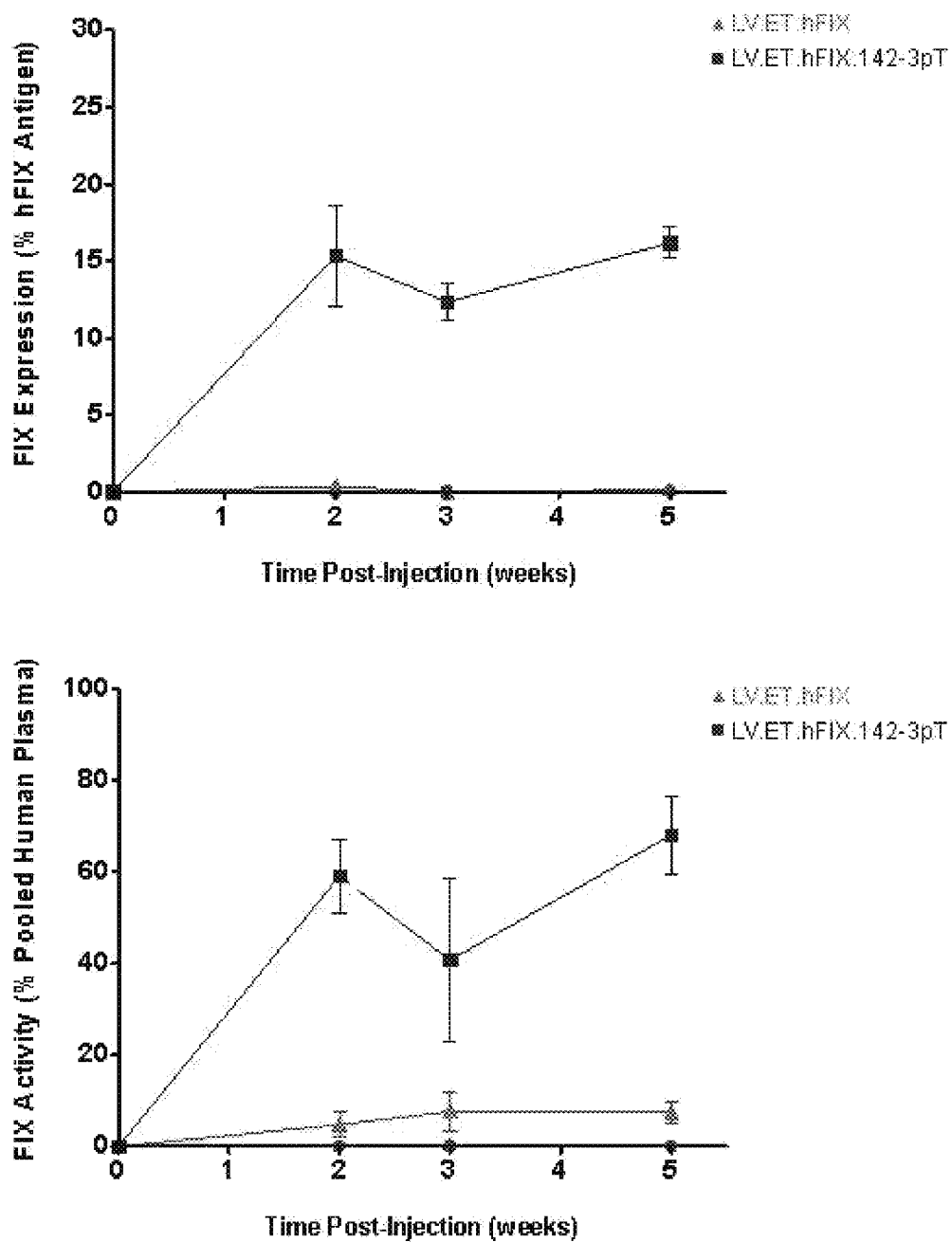
FIG. 8a. miRNA-regulated lentiviral vectors mediate stable correction of hemophilia B in a mouse model. Hemophilia B mice (Factor IX knock-out) were injected via tail with a lentiviral vector encoding hFIX under the control of the hepatocyte-specific ET promoter (LV.ET.hFIX) or a modified LV.ET.hFIX containing the mir-142-3pT sequence in the 3'UTR of the transgene (LV.ET.hFIX.142-3pT). The plasma concentration of hFIX antigen was determined by a hFIX-specific ELISA (top), while FIX clotting activity was determined by measurement of the activated partial thromboplastin time (bottom). Results are presented as the mean plus or minus the standard error from three mice treated per vector.

As a further demonstration of the utility of our approach for establishing long-term transgene expression, we set out to use our system for the treatment of hemophilia B. Hemophilia B mice are completely deficient for clotting FIX, and, as such, they have <1% normal clotting activity. In addition, because they do not naturally express FIX, they are highly prone to developing anti-FIX immunity, upon the introduction of FIX antigens. To circumvent this problem, many groups, including our own, have constructed hepatocyte-specific FIX expression vectors, in order to prevent gene expression in APCs, and avoid the induction of anti-FIX immunity (Brown et al., 2004a; Brown et al., 2004b; Follenzi et al., 2004; Mingozzi et al., 2003). However, as shown in FIG. 8, the hepatocyte-specific LV.ET.hFIX vector was unable to provide long-term FIX expression in hemophilia B mice following intravenous administration. In contrast, injection of the LV.ET.hFIX.142-3pT vector, which contained the mir-142-3pT sequence in the 3'UTR of the FIX expression cassette, resulted in long-term FIX expression, and restored clotting activity to >40% of normal levels.

Overall, these results indicate that using the miRNA-regulated LV, high-level, stable expression of a neo-antigen, whether intracellular or extracellular, can be successfully established in immunocompetent mice, and can even be used to correct the phenotype of a disease, as demonstrated in the hemophilia B mice.

Here we describe the first viral gene transfer system, which exploits the endogenous miRNA machinery for transgene regulation. By using LV-mediated delivery, in vivo gene transfer was possible, and, as such, we provide some of the first in situ data of miRNA activity in an adult mammal. Similar to studies in lower metazoans (Brennecke et al., 2005; Reinhart et al., 2000), we observed miRNA regulation to be extremely efficient. In transgenic mice, as well as mice intravenously administered with LV, we observed consistent mir-142-3p activity in all hematopoietic cells. By adding the mir-142-3pT sequence to a transgene, there was up to a 100-fold reduction in transgene expression in hematopoietic lineages, with no effect on expression in non-hematopoietic cells.

In our system, endogenous miRNA regulation provided a better means for preventing vector expression in hematopoietic lineage cells then the use of the hepatocyte-specific albumin promoter. This most likely occurred because post-transcriptional regulation can overcome off-target expression due to positional effects of insertion and/or imperfect reconstitution of a tissue-specific promoter. This phenomenon may be akin to one of the proposed natural functions of miRNA regulation, which is to prevent translation of mRNAs that were transcribed in a previous cellular state or that arise due to leaky transcription (Bartel and Chen, 2004; Farh et al., 2005). As such, incorporating miRNA regulation into a vector can provide an important layer of control over transgene expression, whether used with ubiquitous promoters or in conjunction with tissue-specific transcription elements.

By using miRNA regulation to de-target transgene expression from hematopoietic lineages, we were able to prevent immune-mediated vector clearance and enablecstable gene transfer, thereby overcoming one of the most significant barriers to clinical gene therapy (Thomas et al., 2003). Of particular relevance, we demonstrate the utility of this approach for both intracellular and extracellular, circulating antigens. Using the miRNA regulation strategy, we were able to achieve stable and high levels of correction of the clotting phenotype of hemophilia B mice. To our knowledge, this is the first demonstration of a therapeutic application to exploit endogenous miRNA regulation.

The studies described here also provide the first evidence that miRNA-mediated regulation is a robust and highly efficient means for virtually abrogating expression from a strong, constitutively active vector promoter, or even for improving the performance of a tissue-specific promoter. Overall, it is clear from this work that miRNAs can provide a powerful way to regulate a transgene, and by utilizing this complex network, we have pioneered a new paradigm in vector design that important implications for therapeutic gene transfer.

Through our approach, which allows for combinatorial mirT arrangements, a variety of gene delivery constructs, whether used in vitro or in vivo, for gene therapy or for animal transgenesis, can be created to achieve sophisticated patterns of gene expression, including the capability to divergently regulate two distinct transgenes. As we continue to discover new tissue-specific, as well as developmental and tumor-specific miRNAs, it will be possible to construct vectors which are conditionally responsive to growth or differentiation and even tumorigenesis.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

REFERENCES

Amendola, M., Venneri, M. A., Biffi, A., Vigna, E., and Naldini, L. (2005). Coordinate dual-gene transgenesis by lentiviral vectors carrying synthetic bidirectional promoters. Nat Biotechnol 23, 108-116.

Barad, O., Meiri, E., Avniel, A., Aharonov, R., Barzilai, A., Bentwich, I., Einav, U., Gilad, S., Hurban, P., Karov, Y., et al. (2004). MicroRNA expression detected by oligonucleotide microarrays: system establishment and expression profiling in human tissues. Genome Res 14, 2486-2494.

Bartel, D. P., and Chen, C. Z. (2004). Micromanagers of gene expression: the potentially widespread influence of metazoan microRNAs. Nat Rev Genet 5, 396-400.

Baskerville, S., and Bartel, D. P. (2005). Microarray profiling of microRNAs reveals frequent coexpression with neighboring miRNAs and host genes. Rna 11, 241-247.

Bender, A., Sapp, M., Schuler, G., Steinman, R. M., and Bhardwaj, N. (1996). Improved methods for the generation of dendritic cells from nonproliferating progenitors in human blood. J Immunol Methods 196, 121-135.

Brennecke, J., Stark, A., Russell, R. B., and Cohen, S. M. (2005). Principles of microRNA-target recognition. PLoS Biol 3, e85.

Brown, B. D., and Lillicrap, D. (2002). Dangerous liaisons: the role of "danger" signals in the immune response to gene therapy. Blood 100, 1133-1140.

Brown, B. D., Shi, C. X., Powell, S., Hurlbut, D., Graham, F. L., and Lillicrap, D. (2004a). Helper-dependent adenoviral vectors mediate therapeutic factor VIII expression for several months with minimal accompanying toxicity in a canine model of severe hemophilia A. Blood 103, 804-810.

Brown, B. D., Shi, C. X., Rawle, F. E., Tinlin, S., McKinven, A., Hough, C., Graham, F. L., and Lillicrap, D. (2004b). Factors influencing therapeutic efficacy and the host immune response to helper-dependent adenoviral gene therapy in hemophilia A mice. J Thromb Haemost 2, 111-118.

Calin, G. A., Liu, C. G., Sevignani, C., Ferracin, M., Felli, N., Dumitru, C. D., Shimizu, M., Cimmino, A., Zupo, S., Dono, M., et al. (2004a). MicroRNA profiling reveals distinct signatures in B cell chronic lymphocytic leukemias. Proc Natl Acad Sci USA 101, 11755-11760.

Calin, G. A., Sevignani, C., Dumitru, C. D., Hyslop, T., Noch, E., Yendamuri, S., Shimizu, M., Rattan, S., Bullrich, F., Negrini, M., and Croce, C. M. (2004b). Human microRNA genes are frequently located at fragile sites and genomic regions involved in cancers. Proc Natl Acad Sci USA 101, 2999-3004.

Chen, C. Z., Li, L., Lodish, H. F., and Bartel, D. P. (2004). MicroRNAs modulate hematopoietic lineage differentiation. Science 303, 83-86.

Chen, C. Z., and Lodish, H. F. (2005). MicroRNAs as regulators of mammalian hematopoiesis. Semin Immunol 17, 155-165.

De Geest, B. R., Van Linthout, S. A., and Collen, 1). (2003). Humoral immune response in mice against a circulating antigen induced by adenoviral transfer is strictly dependent on expression in antigen-presenting cells. Blood 101, 2551-2556.

De Palma, M., Montini, E., de Sio, F. R., Benedicenti, F., Gentile, A., Medico, E., and Naldini, L. (2005). Promoter trapping reveals significant differences in integration site selection between MLV and HIV vectors in primary hematopoietic cells. Blood 105, 2307-2315.

De Palma, M., and Naldini, L. (2002). Transduction of a gene expression cassette using advanced generation lentiviral vectors. Methods Enzymol 346, 514-529.

Doench, J. G., Petersen, C. P., and Sharp, P. A. (2003). siRNAs can function as miRNAs. Genes Dev 17, 438-442.

Farh, K. K., Grimson, A., Jan, C., Lewis, B. P., Johnston, W. K., Lim, L. P., Burge, C. B., and Bartel, D. P. (2005). The widespread impact of mammalian MicroRNAs on mRNA repression and evolution. Science 310, 1817-1821.

Follenzi, A., Battaglia, M., Lombardo, A., Annoni, A., Roncarolo, M. G., and Naldini, L. (2004). Targeting lentiviral vector expression to hepatocytes limits transgene-specific immune response and establishes long-term expression of human antihemophilic factor IX in mice. Blood 103, 3700-3709.

Follenzi, A., Sabatino, G., Lombardo, A., Boccaccio, C., and Naldini, L. (2002). Efficient gene delivery and targeted expression to hepatocytes in vivo by improved lentiviral vectors. Hum Gene Ther 13, 243-260.

Griffiths-Jones, S., Grocock, R. J., van Dongen, S., Bateman, A., and Enright, A. J. (2006). miRBase: microRNA sequences, targets and gene nomenclature. Nucleic Acids Res 34, D140-144.

He, L., and Hannon, G. J. (2004). MicroRNAs: small RNAs with a big role in gene regulation. Nat Rev Genet 5, 522-531.

Houbaviy, H. B., Murray, M. F., and Sharp, P. A. (2003). Embryonic stem cell-specific MicroRNAs. Dev Cell 5, 351-358.

Iorio, M. V., Ferracin, M., Liu, C. G., Veronese, A., Spizzo, R., Sabbioni, S., Magri, E., Pedriali, M., Fabbri, M., Campiglio, M., et al. (2005). MicroRNA gene expression deregulation in human breast cancer. Cancer Res 65, 7065-7070.

Kasashima, K., Sakota, E., and Kozu, T. (2004). Discrimination of target by siRNA: designing of AML1-MTG8 fusion mRNA-specific siRNA sequences. Biochimie 86, 713-721.

Lagos-Quintana, M., Rauhut, R., Yalcin, A., Meyer, J., Lendeckel, W., and Tuschl, T. (2002). Identification of tissue-specific microRNAs from mouse. Curr Biol 12, 735-739.

Lois, C., Hong, E. J., Pease, S., Brown, E. J., and Baltimore, D. (2002). Germline transmission and tissue-specific expression of transgenes delivered by lentiviral vectors. Science 295, 868-872.

Mansfield, J. H., Harfe, B. D., Nissen, R., Obenauer, J., Srineel, J., Chaudhuri, A., Farzan-Kashani, R., Zuker, M., Pasquinelli, A. F., Ruvkun, G., et al. (2004). MicroRNA-responsive 'sensor' transgenes uncover Hox-like and other developmentally regulated patterns of vertebrate microRNA expression. Nat Genet 36, 1079-1083.

Mingozzi, F., Liu, Y. L., Dobrzynski, E., Kaufhold, A., Liu, J. H., Wang, Y., Arruda, V. R., High, K. A., and Herzog, R. W. (2003). Induction of immune tolerance to coagulation factor IX antigen by in vivo hepatic gene transfer. J Clin Invest 111, 1347-1356.

Reinhart, B. J., Slack, F. J., Basson, M., Pasquinelli, A. E., Bettinger, J. C., Rougvie, A. E., Horvitz, H. R., and Ruvkun, G. (2000). The 21-nucleotide let-7 RNA regulates developmental timing in Caenorhabditis elegans. Nature 403, 901-906.

Sandrin, V., Russell, S. J., and Cosset, F. L. (2003). Targeting retroviral and lentiviral vectors. Curr Top Microbiol Immunol 281, 137-178.

Sempere, L. F., Freemantle, S., Pitha-Rowe, I., Moss, E., Dmitrovsky, E., and Ambros, V. (2004). Expression profiling of mammalian microRNAs uncovers a subset of brain-expressed microRNAs with possible roles in murine and human neuronal differentiation. Genome Biol 5, R13.

Steiniger, B., Ruttinger, L., and Barth, P. J. (2003). The three-dimensional structure of human splenic white pulp compartments. J Histochem Cytochem 51, 655-664.

Stripecke, R., Carmen Villacres, M., Skelton, D., Satake, N., Halene, S., and Kohn, D. (1999). Immune response to green fluorescent protein: implications for gene therapy. Gene Ther 6, 1305-1312.

Thomas, C. E., Ehrhardt, A., and Kay, M. A. (2003). Progress and problems with the use of viral vectors for gene therapy. Nat Rev Genet 4, 346-358.

Verma, I. M., and Weitzman, M. D. (2005). GENE THERAPY: Twenty-First Century Medicine. Annu Rev Biochem 74, 711-738.

Zeng, Y., Wagner, E. J., and Cullen, B. R. (2002). Both natural and designed micro RNAs can inhibit the expression of cognate mRNAs when expressed in human cells. Mol Cell 9, 1327-1333.

---

The invention claimed is:

1. A method comprising delivering a gene vector that comprises at least one miRNA target sequence operably linked to a transgene to:
   (i) a cell that comprises a corresponding miRNA, wherein in said cell expression of the transgene is prevented or reduced; and
   (ii) a cell that does not comprise a corresponding miRNA, wherein in said cell the transgene is expressed, wherein the transgene is a therapeutic gene.

2. A method comprising delivering a gene vector that comprises a transgene operably linked to at least one miRNA target sequence to:
   (i) a cell that comprises a corresponding miRNA, thereby preventing immune mediated rejection of the transgene; and
   (ii) a cell that does not comprise a corresponding miRNA, wherein in said cell the transgene is expressed, wherein the transgene is a therapeutic gene.

3. A method for preventing immune-mediated rejection according to claim 2 wherein the transferred gene is a circulating antigen.

4. A method of controlling transgene expression comprising delivering a gene vector that comprises at least one miRNA target sequence operably linked to the transgene to a cell that comprises a corresponding miRNA, wherein in said cell the transgene expression is prevented or reduced, and wherein the transgene is a therapeutic gene.

5. The method of claim 4, wherein the method further comprises delivering the gene vector to a cell that does not comprise a corresponding miRNA, wherein in said cell the transgene is expressed.

6. The method of claim 4, wherein the prevention or reduction of transgene expression in the cell comprising the corresponding miRNA prevents or reduces a detrimental effect to a subject caused by expression of the transgene in said cell.

7. The method of claim 6, wherein the detrimental effect is an immune response to the transgene.

8. A method of de-targeting transgene expression from a type of cell in a subject comprising delivering a gene vector that comprises at least one miRNA target sequence operably linked to the transgene to the subject, wherein upon transduction of a cell that comprises a corresponding miRNA by the gene vector, expression of the transgene is prevented or reduced in said cell, and wherein the transgene is a therapeutic gene.

9. The method of claim 8, wherein upon transduction of a cell that does not comprise a corresponding miRNA by the gene vector, the transgene is expressed in said cell.

10. The method of claim 8, wherein the prevention or reduction of transgene expression in the cell comprising the corresponding miRNA prevents or reduces a detrimental effect to the subject caused by expression of the transgene in said cell.

11. The method of claim 10, wherein the detrimental effect is an immune response to the transgene.

12. A method of controlling transgene expression comprising delivering a gene vector that comprises at least one miRNA target sequence operably linked to a transgene to
a cell that comprises a corresponding miRNA wherein in said cell expression of the transgene is prevented or reduced; and wherein the transgene is a toxic or suicide gene.

\* \* \* \* \*